United States Patent
Patton

(10) Patent No.: US 10,161,584 B2
(45) Date of Patent: Dec. 25, 2018

(54) ELECTRIC LIGHTING DEVICE WITH SCENT CARTRIDGE

(71) Applicant: Luminara Worldwide, LLC, Eden Prairie, MN (US)

(72) Inventor: Douglas Patton, Irvine, CA (US)

(73) Assignee: Luminara Worldwide, LLC, Eden Prairie, MN (US)

( * ) Notice: Subject to any disclaimer, the term of this patent is extended or adjusted under 35 U.S.C. 154(b) by 9 days.

(21) Appl. No.: 15/205,665

(22) Filed: Jul. 8, 2016

(65) Prior Publication Data

US 2017/0067608 A1     Mar. 9, 2017

Related U.S. Application Data

(60) Provisional application No. 62/250,414, filed on Nov. 3, 2015, provisional application No. 62/234,781, filed
(Continued)

(51) Int. Cl.

| | |
|---|---|
| *F21S 6/00* | (2006.01) |
| *F23Q 2/34* | (2006.01) |
| *F21S 10/04* | (2006.01) |
| *A61L 9/12* | (2006.01) |
| *F21V 33/00* | (2006.01) |
| *F21S 9/02* | (2006.01) |

(Continued)

(52) U.S. Cl.
CPC ............. *F21S 10/046* (2013.01); *A61L 9/122* (2013.01); *F21S 6/001* (2013.01); *F21S 9/02* (2013.01); *F21S 10/04* (2013.01); *F21V 23/04* (2013.01); *F21V 23/0442* (2013.01); *F21V 33/0004* (2013.01); *F21V 33/0096* (2013.01); *F23Q 2/345* (2013.01); *A61L 2209/12* (2013.01); *F21Y 2115/10* (2016.08)

(58) Field of Classification Search
CPC .. F21S 10/046; F21S 10/04; F21S 9/02; F21S 6/001; F21Q 2/345
See application file for complete search history.

(56) References Cited

U.S. PATENT DOCUMENTS 5,827,483 A * 10/1998 Fullam ...................... A61L 9/03
                                                  248/166
6,290,914 B1 * 9/2001 LeJeune .............. A01M 1/2088
                                                  422/123
(Continued)

FOREIGN PATENT DOCUMENTS

CA          255031 C     2/2010
CA         2779978 A1    1/2012
(Continued)

*Primary Examiner* — Daniel I Walsh
(74) *Attorney, Agent, or Firm* — Umberg Zipser LLP

(57) ABSTRACT

Electronic lighting systems comprising various internal housing assemblies that provide an air channel for air and scented air are contemplated. In some embodiments, an electronic lighting system comprises a housing disposed within the outer cover that supports a flame element. The flame element is allowed to move on the housing to create a realistic candle light effect. Additionally, a scent cartridge can be inserted into the electronic lighting device to create scented air that moves through an air channel in the electronic lighting device. The scented air is distributed by the electronic lighting device to create an enhanced user experience.

15 Claims, 15 Drawing Sheets

Related U.S. Application Data on Sep. 30, 2015, provisional application No. 62/214,122, filed on Sep. 3, 2015.

(51) Int. Cl.
*F21V 23/04* (2006.01)
*F21Y 115/10* (2016.01)

(56) References Cited

U.S. PATENT DOCUMENTS

| | | | |
|---|---|---|---|
| 6,312,137 B1 | 11/2001 | Hsieh | |
| 6,454,425 B1 | 9/2002 | Lin | |
| 6,461,011 B1 | 10/2002 | Harrison | |
| 6,627,857 B1* | 9/2003 | Tanner | A61L 9/03 219/445.1 |
| 6,955,440 B2 | 10/2005 | Niskanen | |
| 6,966,665 B2 | 11/2005 | Limburg et al. | |
| 7,093,949 B2 | 8/2006 | Hart et al. | |
| 7,159,994 B2 | 1/2007 | Schnuckle et al. | |
| 7,261,455 B2 | 8/2007 | Schnuckle et al. | |
| 7,350,720 B2 | 4/2008 | Jaworski et al. | |
| 7,481,571 B2 | 1/2009 | Bistritzky et al. | |
| 7,503,668 B2* | 3/2009 | Porchia | A01M 1/02 362/161 |
| 7,670,035 B2 | 3/2010 | Tsai | |
| 7,686,471 B2 | 3/2010 | Reichow | |
| 7,824,627 B2 | 11/2010 | Michaels et al. | |
| 7,837,355 B2 | 11/2010 | Schnuckle | |
| 7,997,772 B2 | 8/2011 | Avtzon et al. | |
| 8,070,319 B2 | 12/2011 | Schnuckle et al. | |
| 8,132,936 B2 | 3/2012 | Patton et al. | |
| 8,235,558 B1 | 8/2012 | Lauer | |
| 8,342,712 B2 | 1/2013 | Patton et al. | |
| 8,371,740 B2 | 2/2013 | Pestl et al. | |
| 8,534,869 B2 | 9/2013 | Patton et al. | |
| 8,550,660 B2 | 10/2013 | Patton et al. | |
| 8,628,223 B2 | 1/2014 | Kwok et al. | |
| 8,646,946 B2 | 2/2014 | Schnuckle et al. | |
| 8,696,166 B2 | 4/2014 | Patton et al. | |
| 8,721,118 B2 | 5/2014 | Patton et al. | |
| 8,727,569 B2 | 5/2014 | Schnuckle et al. | |
| 8,783,888 B2 | 7/2014 | McCavit et al. | |
| 8,789,986 B2 | 7/2014 | Li | |
| 8,844,837 B1* | 9/2014 | Pesu | A61L 9/127 239/289 |
| 8,926,137 B2 | 1/2015 | Li | |
| 9,033,553 B2 | 5/2015 | Li | |
| 9,052,087 B2 | 6/2015 | Sheng | |
| 9,074,759 B2 | 7/2015 | Lai | |
| 9,192,690 B2 | 11/2015 | Zobele | |
| 10,010,640 B1* | 7/2018 | Li | A61L 9/03 |
| 2002/0066798 A1* | 6/2002 | Laudamiel-Pellet | A01M 1/2033 239/34 |
| 2002/0068009 A1* | 6/2002 | Laudamiel-Pellet | A01M 1/2033 422/5 |
| 2002/0158351 A1* | 10/2002 | Wohrle | A61L 9/035 261/142 |
| 2002/0197188 A1* | 12/2002 | Lua | A61L 9/12 422/124 |
| 2003/0020185 A1* | 1/2003 | Cox | A01M 1/2033 261/26 |
| 2003/0026088 A1* | 2/2003 | Vanderschuit | A47G 19/2222 362/101 |
| 2003/0053305 A1 | 3/2003 | Lin | |
| 2003/0198054 A1 | 10/2003 | Kitchen | |
| 2004/0165374 A1 | 8/2004 | Robinson | |
| 2004/0196658 A1 | 10/2004 | Fung | |
| 2004/0257798 A1 | 12/2004 | Hart et al. | |
| 2005/0036317 A1* | 2/2005 | Niskanen | F21S 9/02 362/294 |
| 2005/0073833 A1* | 4/2005 | VanderSchuit | A47G 19/2222 362/101 |
| 2005/0116059 A1* | 6/2005 | Lin | A61L 9/14 239/102.2 |
| 2005/0169666 A1* | 8/2005 | Porchia | A01M 1/02 399/111 |
| 2005/0169812 A1* | 8/2005 | Helf | A01M 1/02 422/123 |
| 2005/0195598 A1* | 9/2005 | Dancs | A61L 9/037 362/231 |
| 2005/0285538 A1 | 12/2005 | Jaworski et al. | |
| 2006/0034100 A1 | 2/2006 | Schnuckle et al. | |
| 2006/0115386 A1* | 6/2006 | Michaels | A01M 1/205 422/123 |
| 2006/0120080 A1* | 6/2006 | Sipinski | A01M 1/205 362/253 |
| 2006/0125420 A1 | 6/2006 | Boone et al. | |
| 2006/0188238 A1* | 8/2006 | Kent | A61L 9/03 392/394 |
| 2006/0221594 A1* | 10/2006 | Thuot Rann | A61L 9/037 362/96 |
| 2006/0283405 A1* | 12/2006 | Chou | A61H 33/063 122/32 |
| 2007/0003894 A1* | 1/2007 | Yu | F21S 6/001 431/289 |
| 2007/0127249 A1 | 6/2007 | Medley et al. | |
| 2008/0031784 A1* | 2/2008 | Bistritzky | A01M 1/2033 422/124 |
| 2008/0036332 A1* | 2/2008 | Helf | B05B 17/0646 310/311 |
| 2008/0038156 A1* | 2/2008 | Jaramillo | A01M 1/2072 422/124 |
| 2008/0112154 A1 | 5/2008 | Reichow | |
| 2008/0130266 A1 | 6/2008 | DeWitt et al. | |
| 2008/0150453 A1 | 6/2008 | Medley et al. | |
| 2008/0197213 A1* | 8/2008 | Flashinski | A01M 1/205 239/288.5 |
| 2008/0279731 A1* | 11/2008 | Goreham | A61L 9/037 422/125 |
| 2008/0311008 A1* | 12/2008 | Tranzeat | A01M 1/2033 422/124 |
| 2008/0315005 A1* | 12/2008 | Michaels | A01M 1/2033 239/4 |
| 2009/0302128 A1 | 12/2009 | Zobele | |
| 2010/0124050 A1* | 5/2010 | Hau | H02J 50/10 362/183 |
| 2010/0283407 A1* | 11/2010 | Demarest | H05B 33/0815 315/294 |
| 2010/0284168 A1 | 11/2010 | Walter et al. | |
| 2011/0019422 A1* | 1/2011 | Schnuckle | F21S 10/04 362/277 |
| 2011/0027124 A1 | 2/2011 | Albee et al. | |
| 2011/0031887 A1* | 2/2011 | Stoll | F21V 29/004 315/113 |
| 2011/0079660 A1* | 4/2011 | Jorgensen | A61L 9/14 239/144 |
| 2011/0089252 A1* | 4/2011 | Rosener | A01M 1/2044 239/6 |
| 2011/0110073 A1* | 5/2011 | Schnuckle | F21S 10/04 362/96 |
| 2011/0127914 A1 | 6/2011 | Patton et al. | |
| 2011/0134628 A1* | 6/2011 | Pestl | F21V 33/004 362/96 |
| 2011/0156288 A1* | 6/2011 | Ahn | F24F 6/12 261/30 |
| 2011/0221078 A1* | 9/2011 | Lev | A61L 9/03 261/81 |
| 2011/0239539 A1* | 10/2011 | Gatt | F23D 3/02 48/61 |
| 2011/0255272 A1 | 10/2011 | Privas | |
| 2012/0020052 A1 | 1/2012 | McCavit et al. | |
| 2012/0024837 A1 | 2/2012 | Thompson | |
| 2012/0093491 A1 | 4/2012 | Browder et al. | |
| 2012/0134157 A1 | 5/2012 | Li | |
| 2012/0183280 A1* | 7/2012 | Kowalec | A61L 9/03 392/386 |
| 2012/0300433 A1* | 11/2012 | Lee | F21V 33/00 362/96 |

(56) References Cited

U.S. PATENT DOCUMENTS

| | | |
|---|---|---|
| 2013/0050985 A1 | 2/2013 | Kwok et al. |
| 2013/0148353 A1 | 6/2013 | Patton et al. |
| 2013/0258648 A1 | 10/2013 | Ding |
| 2013/0286642 A1 | 10/2013 | Patton |
| 2014/0049941 A1* | 2/2014 | Lee .................. A61L 9/122 362/96 |
| 2014/0177212 A1 | 6/2014 | Li |
| 2014/0218929 A1 | 8/2014 | Schnuckle et al. |
| 2014/0227141 A1* | 8/2014 | Chen ................. A61L 9/037 422/125 |
| 2014/0268652 A1* | 9/2014 | Li ..................... F21S 10/04 362/96 |
| 2014/0286024 A1* | 9/2014 | Li ..................... F21S 10/04 362/392 |
| 2014/0313694 A1 | 10/2014 | Patton et al. |
| 2015/0109786 A1 | 4/2015 | Li |
| 2015/0257443 A1* | 9/2015 | Rado .................. A24F 47/00 392/390 |
| 2015/0285453 A1 | 10/2015 | Schnuckle et al. |
| 2015/0292695 A1 | 10/2015 | Schnuckle et al. |
| 2015/0328353 A1* | 11/2015 | Schramm ............ A61L 9/02 392/393 |
| 2015/0338087 A1* | 11/2015 | Fang ................... F24F 3/056 362/96 |
| 2015/0373815 A1* | 12/2015 | Patton ............... F21V 33/0052 315/297 |
| 2016/0047517 A1 | 2/2016 | Li |
| 2016/0109081 A1* | 4/2016 | Thompson ........... F21S 10/046 362/96 |
| 2016/0109082 A1 | 4/2016 | Li |
| 2016/0109083 A1 | 4/2016 | Li |
| 2016/0258584 A1* | 9/2016 | Li ..................... F21S 10/04 |
| 2016/0338412 A1* | 11/2016 | Monsees ............. A24F 47/008 |
| 2017/0067608 A1* | 3/2017 | Patton ................ F21S 10/046 |
| 2017/0072084 A1* | 3/2017 | Gruenbacher ......... A61L 9/032 |
| 2017/0157281 A1* | 6/2017 | Ma ..................... A61L 9/14 |
| 2017/0184300 A1* | 6/2017 | Liu ..................... A61L 9/14 |
| 2017/0211767 A1* | 7/2017 | Baeza ................ F21S 10/046 |
| 2017/0274405 A1* | 9/2017 | Lucas ................ B05B 17/0646 |
| 2017/0292666 A1* | 10/2017 | Li ..................... F21S 10/04 |
| 2018/0066840 A1* | 3/2018 | Bianchini ............. F23Q 3/00 |

FOREIGN PATENT DOCUMENTS

| | | |
|---|---|---|
| CA | 2886665 A1 | 1/2012 |
| CN | 2524064 Y | 12/2002 |
| CN | 201344443 Y | 11/2009 |
| CN | 201724143 U | 1/2011 |
| CN | 102563510 A | 7/2012 |
| CN | 102734740 A | 10/2012 |
| CN | 202647570 U | 1/2013 |
| CN | 103196094 A | 7/2013 |
| CN | 102721002 B | 6/2014 |
| EP | 1878449 A1 | 1/2008 |
| EP | 1639291 B1 | 5/2009 |
| EP | 2565518 A1 | 3/2013 |
| EP | 2587127 A1 | 5/2013 |
| GB | 2323159 A | 9/1998 |
| GB | 2379731 A | 3/2003 |
| WO | 2006/020839 A2 | 2/2006 |
| WO | 2008/016867 A2 | 2/2008 |
| WO | 2010/039347 A1 | 4/2010 |
| WO | 2011/112258 A1 | 9/2011 |
| WO | 2013/198187 A1 | 12/2013 |
| WO | 2014/062831 A2 | 4/2014 |
| WO | 2015/080664 A1 | 6/2015 |

\* cited by examiner

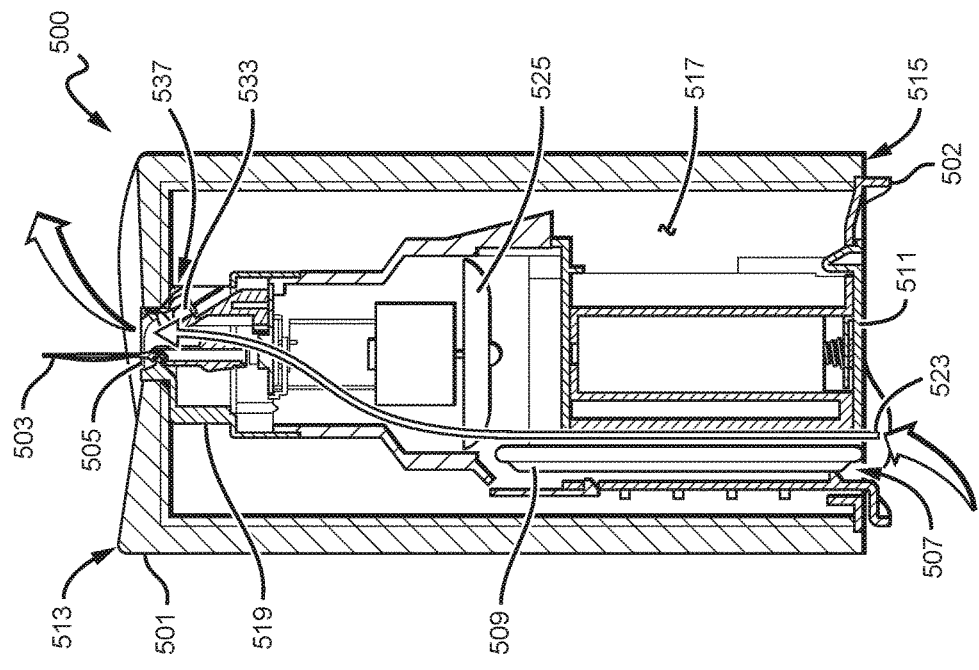
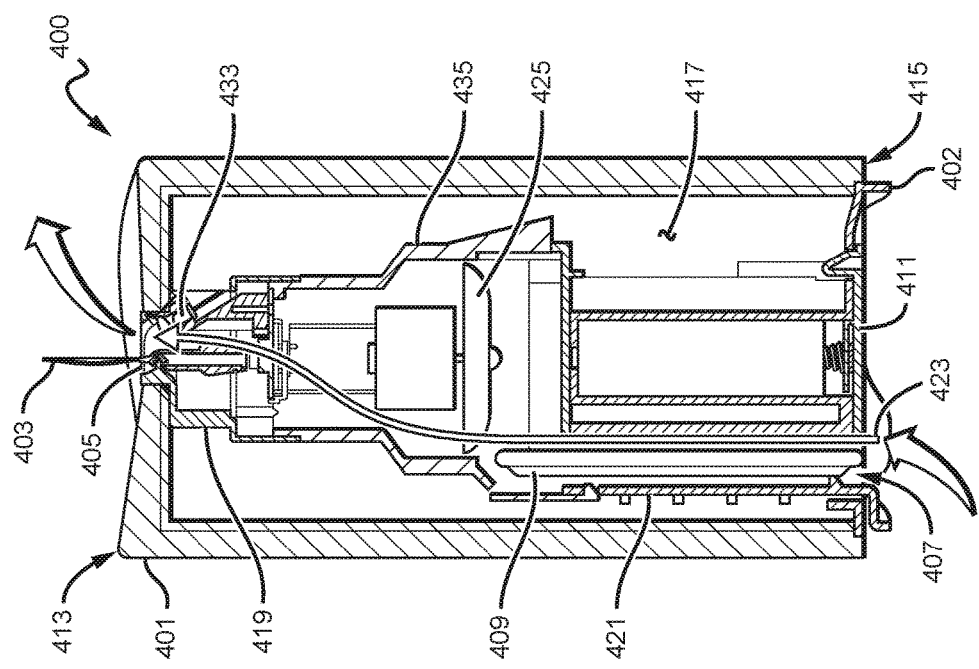

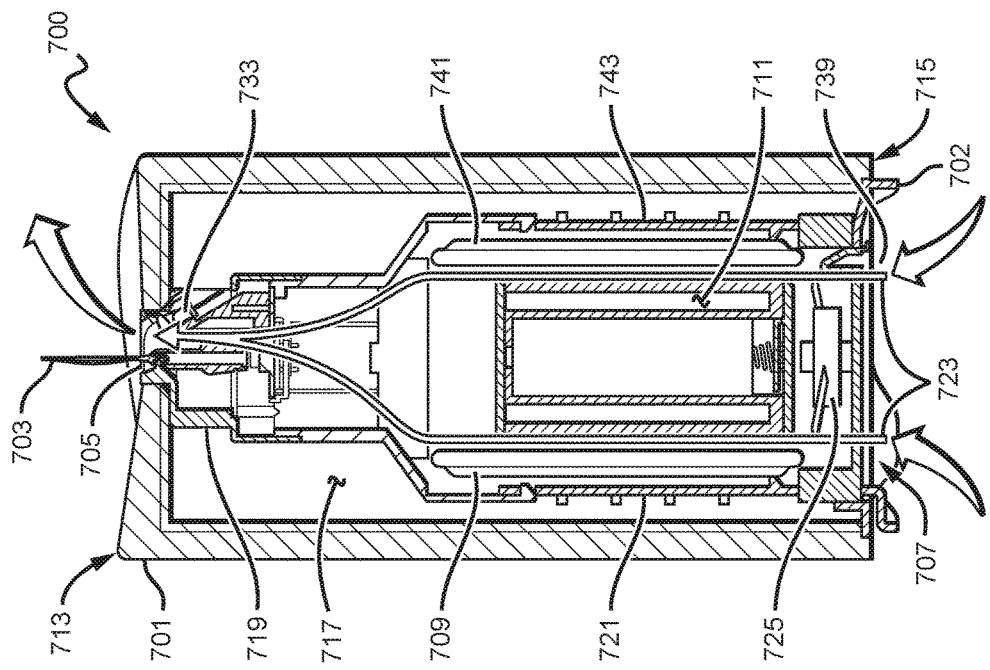
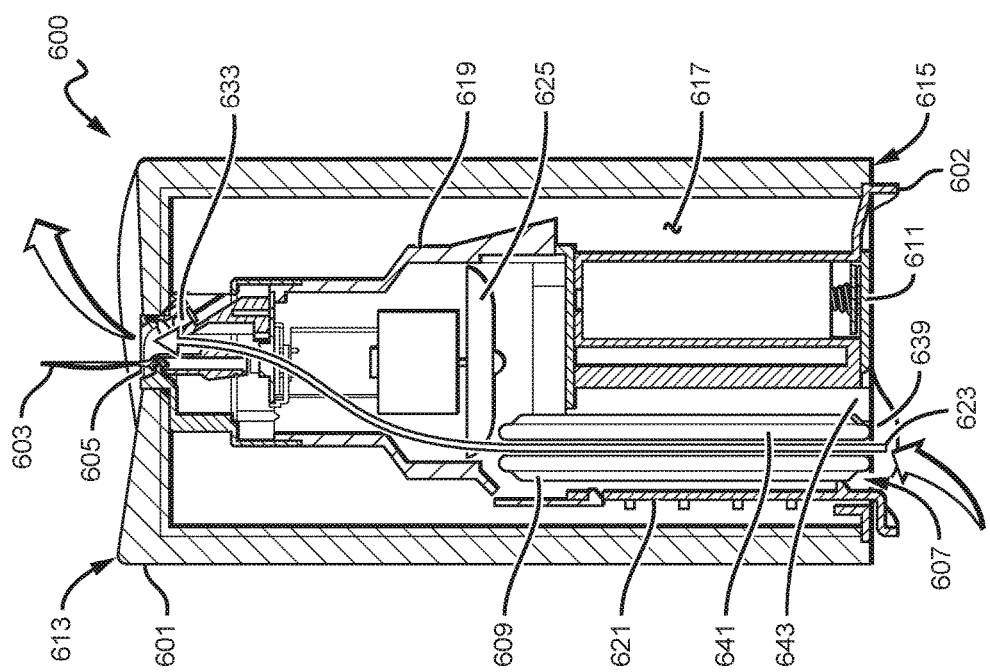

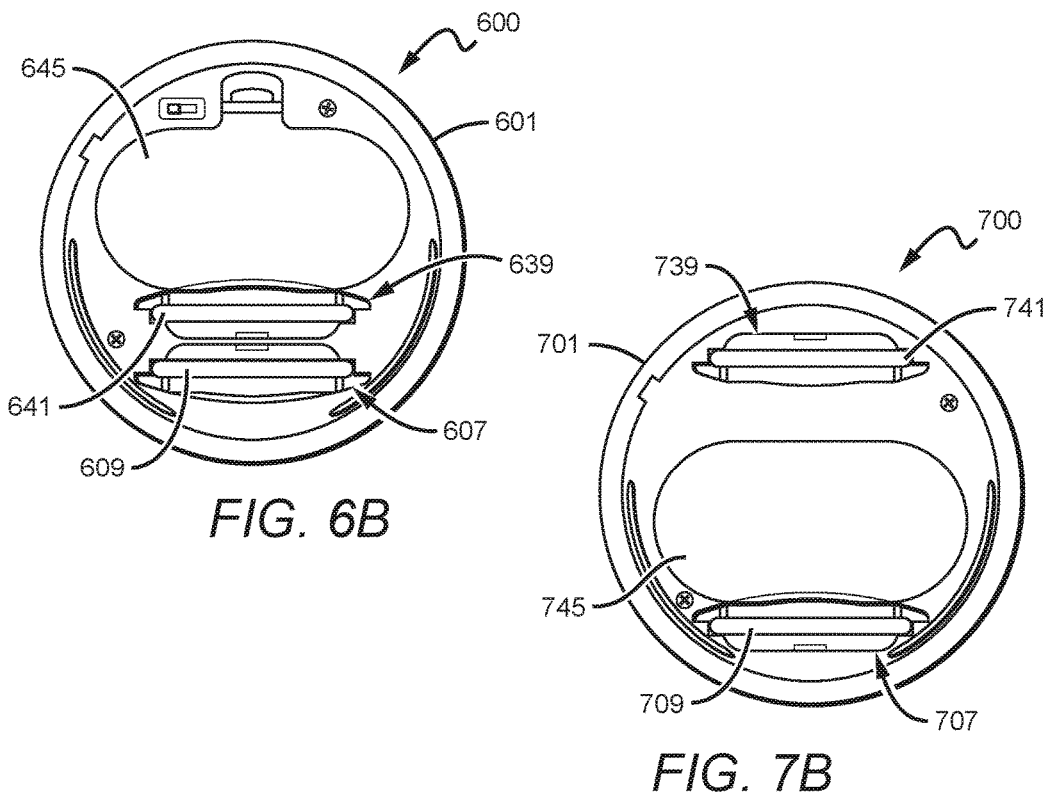
FIG. 6B
FIG. 7B
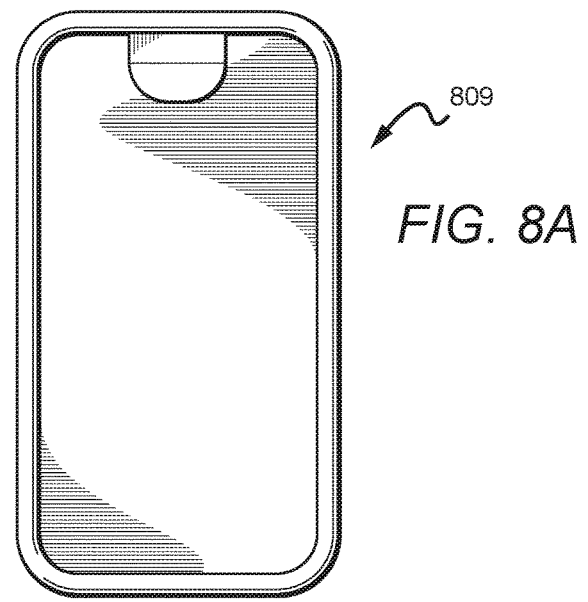
FIG. 8A

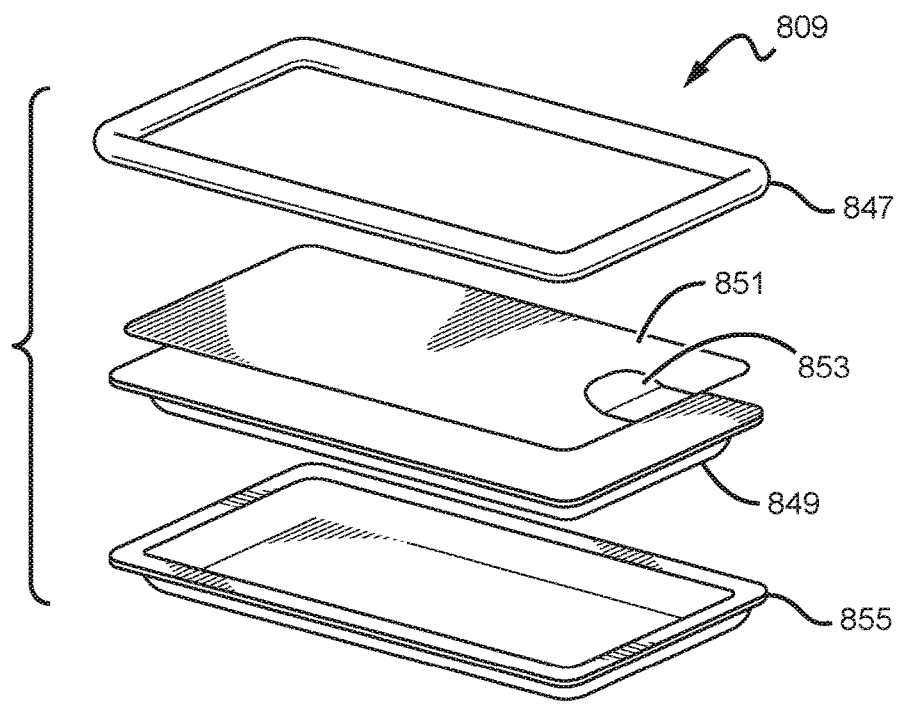
FIG. 8B
FIG. 8C
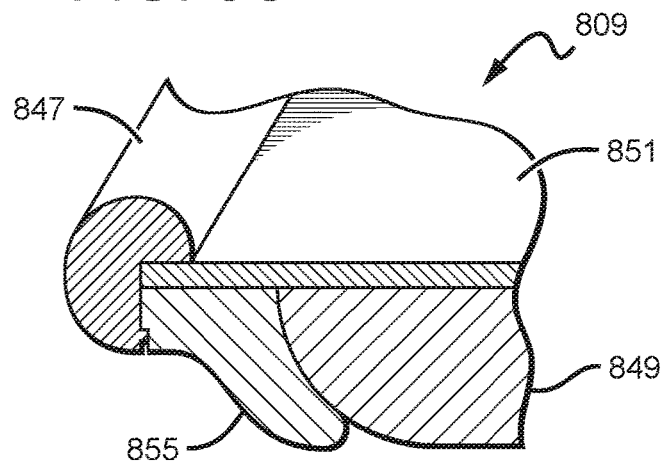

ELECTRIC LIGHTING DEVICE WITH SCENT CARTRIDGE

This application claims priority to U.S. Provisional Application No. 62/250,414, filed Nov. 3, 2015, U.S. Provisional Application No. 62/234,781, filed Sep. 30, 2015, and U.S. Provisional Application No. 62/214,122, filed Sep. 3, 2015. All extrinsic materials identified herein are incorporated by reference in their entirety.

FIELD OF THE INVENTION

The field of the invention is electronic candles having replaceable scent cartridges.

BACKGROUND

The background description includes information that may be useful in understanding the present invention. It is not an admission that any of the information provided herein is prior art or relevant to the presently claimed invention, or that any publication specifically or implicitly referenced is prior art.

Electronic lighting devices are convenient tools that provide light when needed. These tools can have a simple design, such as a flashlight, or an ornamental design, such as a flameless candle. Regardless of the design, many electronic lighting devices are limited to the function of providing light. Although having a single function can be beneficial in reducing the complexity of creating electronic lighting devices, such an overly simplistic lighting device can be problematic for users that desire additional functionalities.

Some have contemplated creating an electronic lighting device that emits fragrances. See, e.g., U.S. Pat. No. 8,371,740 to Pestl et al.; U.S. Pat. No. 8,783,888 to McCavit et al.; U.S. Pat. No. 7,350,720 to Jaworski et al.; U.S. Pat. No. 6,966,665 to Limburg et al.; WO 2014/062831 to Thompson et al.; US 2005/0285538 to Jaworski et al.; U.S. Pat. No. 7,481,571 to Bistritzky et al.; US 2008/0031784 to Bistritzky et al.; US 2006/0125420 to Boone et al.; US 2007/0127249 to Medley et al.; US 2008/0150453 to Medley et al.; US 2005/0169666 to Porchia, et al.; U.S. Pat. No. 7,503,668 to Porchia, et al.; U.S. Pat. No. 7,824,627 to Michaels, et al.; US 2006/0039835 to Nottingham et al.; US 2008/0038156 to Jaramillo; US 2008/0130266 to DeWitt et al.; US 2012/0024837 to Thompson; US 2011/0027124 to Albee et al.; and US 2012/0093491 to Browder et al. However, there are still disadvantages with the many of the references noted above.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Thus, there is still a need for improved electronic lighting devices that provide additional functionality.

SUMMARY OF THE INVENTION

The inventive subject matter provides apparatus, systems, and methods in which electronic lighting devices can simulate a real candle light flame while providing a scent to thereby enhance a user's experience. In contemplated embodiments, an electronic lighting device comprises an outer cover having a top end and a bottom end that at least partially define an internal cavity. A housing having an aperture is disposed within the internal cavity at the top end. A flame element extends through the aperture and is supported by the housing, such that flame element can move freely to simulate a real candle flame. An air channel is disposed from a first end to a second end, and more preferably, the top end to the bottom end, and is configured to direct airflow from the bottom end to the top end or the top end to the bottom end in some embodiments.

The electronic lighting device comprises a slot that is configured to receive one or more scent cartridges. A fan is configured to move air through the air channel. When a scent cartridge is inserted in the slot, the fan can be used to move air and scented air through the air channel to release a fragrance from the device. Thus, it should be appreciated that electronic lighting devices can be produced to provide lighting and scented air whereby the scented air can be easily modified by replacing the scent cartridge in the electronic lighting device.

The electronic lighting devices can be assembled using various components and couplings. For example, it is contemplated that the air channel is formed by a coupling the housing and a scent cartridge housing. In this two-part assembly, the fan can be disposed in the housing, and the housing and scent cartridge housing couple to form the air channel. In a three-part assembly, the fan can be disposed in a fan housing, and the housing, the fan housing, and the scent cartridge housing couple to form the air channel. In a four-part assembly, the electronic lighting device can further comprise a battery compartment, and the housing, the fan housing, the scent cartridge housing, and the battery compartment couple to form the air channel. It should be appreciated that all combinations of couplings between at least two of the housing, the fan housing, the scent cartridge housing, and the battery compartment are contemplated. Moreover, in other embodiments, it is contemplated that electronic lighting device consists of a single piece, injection-molded housing (i.e., no other housings (fan housing, battery compartment, scent cartridge housing, etc.) couple to the housing) having compartments, openings, and/or recesses to house all the various components (e.g., fan, scent cartridge, batteries, light source, etc.).

The housing can comprise an arm that is affixed to the housing, and the arm can support movement of the flame element within the housing. The flame element typically comprises a hollow interior having a projection that extends into the hollow interior. The arm comprises a recess that is configured to receive the projection to thereby support the flame element within the housing. It should be noted that the movement of the flame element on the arm creates a realistic flame effect to simulate a real candle light. The movement of the flame element can be generated using various mechanisms. For example, an electromagnet coil can be disposed within the housing to generate an electromagnetic field, which interacts with a ferrous material or a magnet disposed on the flame element to cause movement to the flame element. However, the flame element could be mounted in all other manners without departing from the scope of the invention.

The fan can be coupled to a fan controller that is preferably configured to vary a speed of the fan as a function of time. In preferred embodiments, the fan operates at full speed when powered on, then the fan stops operation, and then the fan restarts operation at a reduced speed, likely between 50-80% of full speed. For example, the fan controller can be configured to operate the fan at 100% speed for a first amount of time followed by 0% speed for a second amount of time and followed by less than 100% speed for a third amount of time to thereby maintain scent. The first amount of time can be 1-15 minutes, and preferably between 1-3 minutes, the second amount of time can be 1-10 minutes, and preferably between 1-5 minutes, and the third amount of time can be for the remaining time that the fan is on or a set time period. Thus, fan controller can operate fan to quickly disperse scented air when a scent cartridge is placed in the electronic lighting device, and the fan speed can be modified to maintain a steady state of dispersion of scented air.

The scent cartridge housing can have many suitable mechanisms to lock a scent cartridge within a slot on the scent cartridge housing. For example, it is contemplated that the scent cartridge housing can comprise a slide door, a flap door, or a pivot lock to secure the scent cartridge within the slot. In some embodiments, the scent cartridge housing can comprise a battery compartment configured to receive a battery. However, it is also contemplated that the battery compartment is a separate unit from the scent cartridge housing.

Electronic lighting devices can further comprise a second scent cartridge housing having a second slot to receive a second scent cartridge. The first scent cartridge and the second scent cartridge can be of the same or similar scent, and it is also contemplated that the first and second scent cartridges can be different scents that can combine to create a unique blended scent. In still further embodiments, two or more scent cartridges can be disposed in one slot, or multiple scents can be disposed in a single scent cartridge (e.g., a single cartridge can have a plurality of slots with each slot have a different scent).

In addition to having various housings (e.g., housing, fan housing, scent cartridge housing, battery compartment, etc.) that can couple to form an electronic lighting device as discussed above, it is contemplated that the orientation of the various housings can vary with respect to one another. For example, the fan can be disposed on the bottom end of the outer cover, and the scent cartridge housing and/or the second scent cartridge housing can be disposed between the fan and the housing. In another example, the scent cartridge housing and/or the second scent cartridge housing can be disposed on the bottom end of the outer cover, and the fan can be disposed between the scent cartridge housing and/or the second scent cartridge housing and the housing. In yet another example, the scent cartridge housing is adjacent to the second scent cartridge housing or a battery compartment can be disposed between the scent cartridge housing and the second scent cartridge housing.

The scent cartridge can comprise a scent pack that is housed within a frame. A removable cover can be disposed on the scent pack that can be removed to thereby allow scent to be disposed from the scent pack. Moreover, it is contemplated that the scent cartridge can comprise a male or female connector that is configured to couple with a male or female connector on the scent cartridge housing to hold scent cartridge within the slot of the scent cartridge housing.

In another aspect, an electronic lighting device having an outer cover with a top end and a bottom end that at least partially define an internal cavity is contemplated. A housing is disposed within the internal cavity at the top end, and the housing comprises an aperture. A fan is disposed within the outer cover, and a slot that is configured to receive a scent cartridge is disposed on the bottom end. An air channel is disposed from the top end to the bottom end, wherein the slot forms a first opening of the air channel and the aperture forms a second opening of the air channel.

The electronic lighting device can comprise a second slot configured to receive a second scent cartridge that forms a third opening of the air channel. The slot and second slot can be adjacent to one another or a battery compartment can be disposed between the slot and the second slot.

As discussed in the embodiments above, the electronic lighting device can be composed of a plurality of housings (e.g., housing, battery compartment, scent cartridge housing, fan housing, second scent cartridge housing, etc.) that couple one another to house the various components (e.g., fan, scent cartridge, battery, light source, etc.) within the electronic lighting device. However, it is also contemplated that the electronic lighting device can have a housing that is a single unit (i.e., no other housings (fan housing, battery compartment, scent cartridge housing, etc.) couple to the housing), which houses the fan and the other components, and comprises the slot.

In yet another aspect, an electronic lighting device having an outer cover with a top end and a bottom end that at least partially define an internal cavity is contemplated. A housing is disposed within the internal cavity, wherein the housing extends from the top end to the bottom end of the outer cover. Typically, the housing is a single unit (i.e., no other housings (fan housing, battery compartment, scent cartridge housing, etc.) couple to the housing) that houses the various components within the electronic lighting device. A flame element extends through an aperture of the housing and is supported by an arm of the housing. A slot is disposed on the bottom end of the housing, and is configured to receive a scent cartridge. An air channel is disposed from the top end to the bottom end and configured to direct airflow from the bottom end to the top end.

The housing can be formed as a single unit by injection molding. As briefly discussed above, the housing can be a single unit that provides housing for the fan, the scent cartridge, a battery, the light source, and other components within the electronic lighting device. The housing can have an outer surface that abuts an inner surface of the outer cover when the housing is disposed within the outer cover. This abutment can assist in channeling the airflow through the air channel as opposed to having airflow in the internal cavity between the outer surface of the housing and the inner surface of the outer cover.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 4 is a cross-sectional view of an embodiment of an electronic lighting device.

FIG. 5 is a cross-sectional view of an embodiment of an electronic lighting device.

FIG. 6A is a cross-sectional view of an embodiment of an electronic lighting device.

FIG. 6B is a bottom view of the electronic lighting device in FIG. 6A.

FIG. 7A is a cross-sectional view of an embodiment of an electronic lighting device.

FIG. 7B is a bottom view of the electronic lighting device in FIG. 7A.

FIG. 8A is a perspective view of an embodiment of a scent cartridge.

FIG. 8B is an exploded view of the scent cartridge in FIG. 8A.

FIG. 8C is an enlarged view of an area of the scent cartridge in FIG. 8A.

DETAILED DESCRIPTION

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Also, as used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The inventors have discovered improved electronic lighting devices that simulate a real candle and also provide a scented aroma to thereby increase the usefulness of typical electronic lighting devices. Moreover, the scented aroma can be easily modified by removing a scent cartridge from the electronic lighting device, and replacing the scent cartridge with a second scent cartridge. In some embodiments, multiple scent cartridges can be disposed within the electronic lighting device to provide at least one of (i) a stronger scent using two of the same or similar scent cartridges, (ii) a blended scent using two similar or distinct scent cartridges, (iii) a selection of scents, and (iv) a backup scent cartridge by having a first scent cartridge being used and providing a second scent cartridge that remains idle until the first scent cartridge is consumed. Thus, it should be appreciated that electronic lighting devices can provide the dual functionality of real candle simulation and fragrance dispersion, and, in addition, allow for simple customization of the electronic lighting device by interchanging scent cartridges to create unique scents.

Figure 1A:
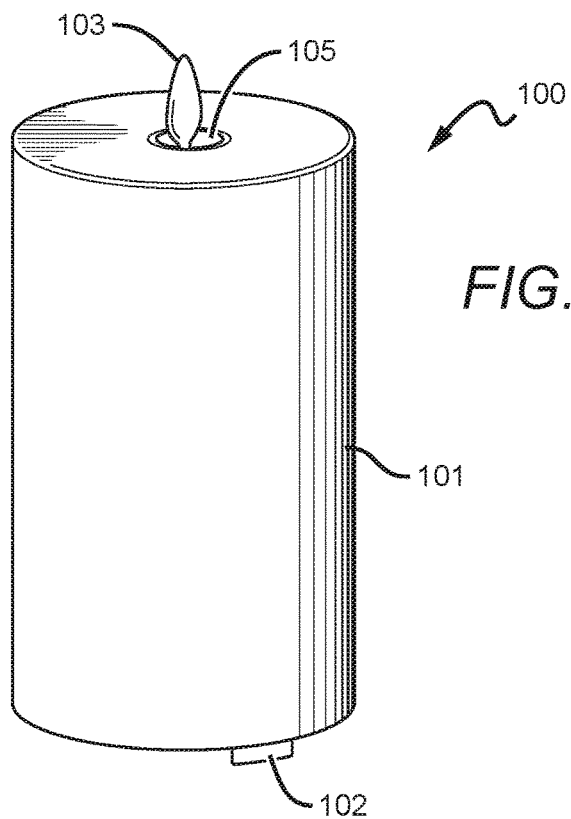
FIG. 1A is a perspective view of an embodiment of an electronic lighting device.

FIG. 1A shows an electronic lighting device 100 having an outer cover 101. A flame element 103 extends through an aperture 105 on a top of electronic lighting device 100, and is allowed to move in a manner that simulates a moving flame of a real candle. The mechanism that creates motion of flame element 103 can vary. For example, a circuit board can drive a drive mechanism, which could be an electromagnet, a fan, or other component that creates kinetic motion of flame element 103 to simulate the movement of a moving flame. In another example, an electromagnet coil can be disposed within the housing that is configured to generate an electromagnetic field, which interacts with a ferrous material or a magnet disposed on the flame element to cause movement to flame element 103. A detailed description of exemplary internal configurations that are configured to move a flame element in an electronic lighting device can be found in PCT International Application No. PCT/US2015/011642, which is hereby incorporated by reference.

Aperture 105 is typically disposed on a housing that supports flame element 103. In contemplated embodiments, aperture 105 can provide an exit point for scented air from inside of electronic lighting device 100. However, it is also contemplated that aperture 105 can be an ingress point for air to enter electronic lighting device 100.

Following aperture 105 downward into electronic lighting device 100 is an air channel that flows through electronic lighting device 100 and through a bottom opening of electronic lighting device 100. A scent distributor, which is preferably a fan, can move air through the air channel. It is contemplated scent distributor can be any other mechanism capable of causing air to move (e.g., a heating mechanism that causes hot air to rise).

Electronic lighting device 100 can also have one or more legs 102 that provides a space between a bottom of electronic lighting device 100 and a surface (e.g., tabletop, desktop, and any other solid surface) that supports electronic lighting device 100. The space can provide an area for air to travel, and in some embodiments, air can travel through the space and into a bottom of electronic lighting device 100 to produce scented air. In other embodiments, it is contemplated that electronic lighting device 100 does not have any legs, such that the bottom of electronic lighting device 100 lies flat on a surface.

Figure 1B:
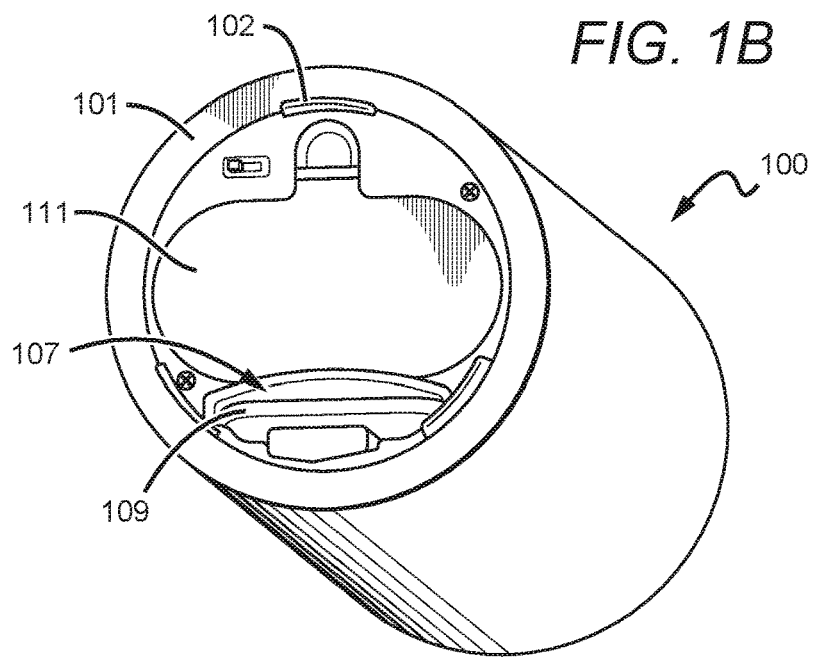
FIG. 1B is a bottom perspective view of the electronic lighting device in FIG. 1A.

The bottom of electronic lighting device 100 is shown in FIG. 1B. Electronic lighting device 100 can comprise a slot 107 that is configured to receive a scent cartridge 109. Slot 107 can also provide an exit point or an ingress point for air to move through an air channel in electronic lighting device 100. As air moves through the air channel, it comes into contact with scent cartridge thereby producing scented air. Although slot 107 is shown on the bottom of electronic lighting device 100 near a battery compartment 111, it is contemplated that slot 107 can be disposed on a side, within, or on a top of electronic lighting device 100. In embodiments where batteries in the battery compartment are cylindrical, it is contemplated that the two batteries next to one another naturally create an air channel.

Figure 1C:
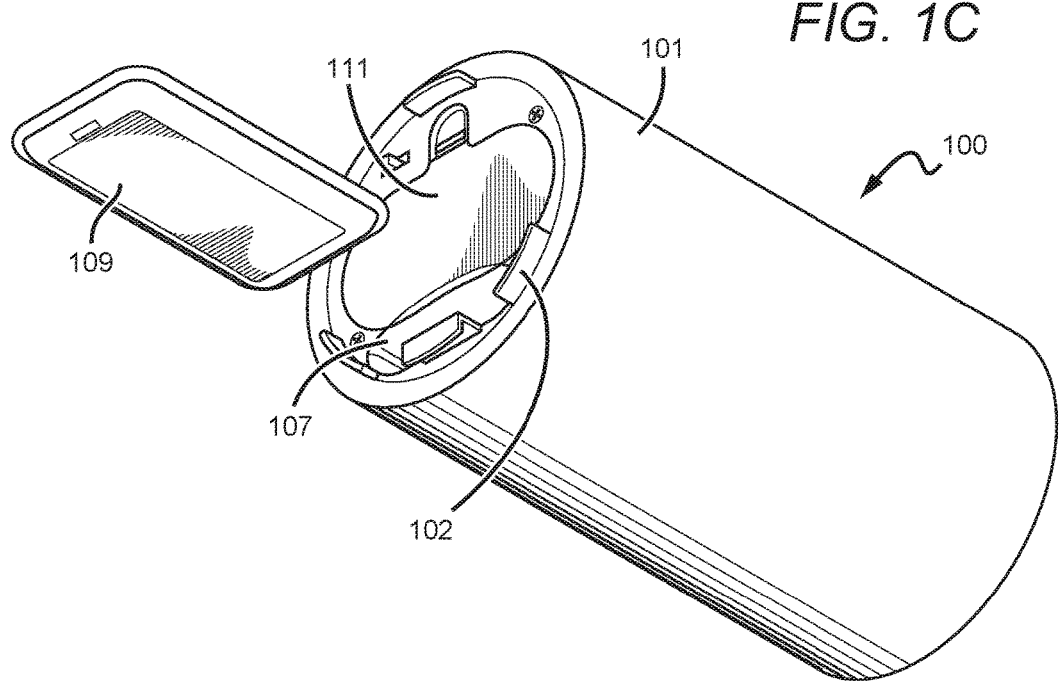
FIG. 1C is a bottom perspective view of the electronic lighting device in FIG. 1A.

FIG. 1B shows scent cartridge 109 inserted in slot 107 of electronic lighting device 100. Once inserted, the scent cartridge 109 can be held in place by any one of a fastener, an adhesive, a latch, a detent, or any other mode of holding two components together. It is also contemplated that slot 107 can additionally comprise spring components to facilitate insertion and extraction. For example, a spring can provide resistance to insertion, and can be used to push the scent cartridge 109 back out when desired. FIG. 1C shows scent cartridge 109 removed from electronic lighting device 100. As discussed above, it is contemplated that one or more scent cartridges can be inserted and/or removed from electronic lighting device 100. With respect to similarly numbered numerals (e.g., 103, 203, 303, etc.), it is contemplated that the features described in one embodiment can be incorporated in other embodiments.

Figure 2B:
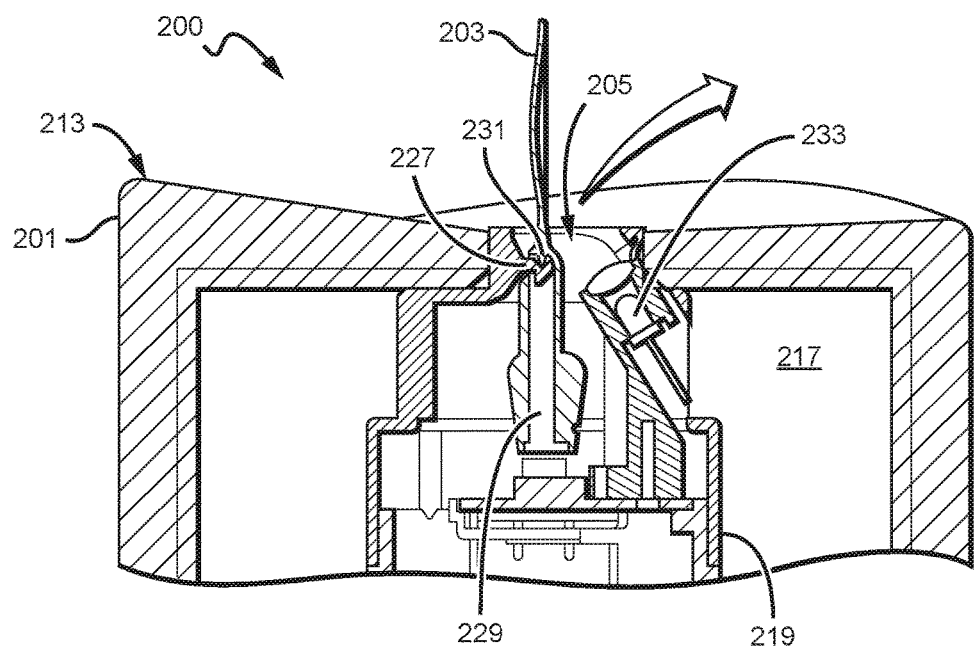
FIG. 2B is an enlarged view of a section of the electronic lighting device in FIG. 2A.
Figure 2A:
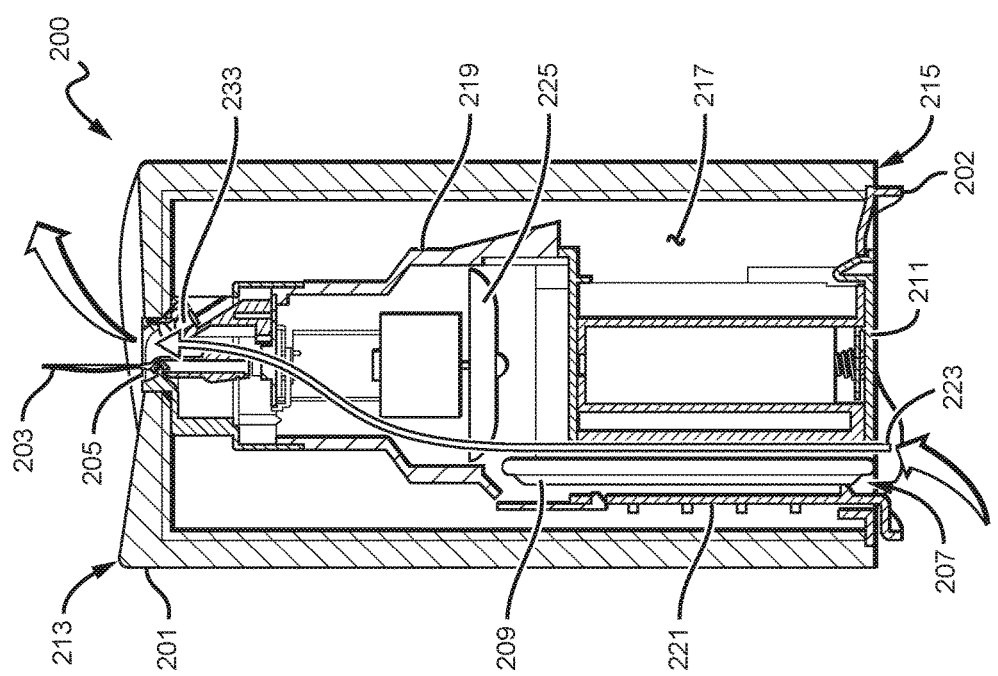
FIG. 2A is a cross-sectional view of an embodiment of an electronic lighting device.

FIG. 2A shows an embodiment of an electronic lighting device 200. Electronic lighting device 200 comprises an outer cover 201 having a top end 213 and a bottom end 215 that define an internal cavity 217. In other embodiments, outer cover 201 can partially define internal cavity 217 instead of completely defining internal cavity 217. A housing 219 is typically disposed within internal cavity 217 and comprises an aperture 205. A flame element 203 extends through aperture 205 and is supported by housing 219.

Electronic lighting device 200 also comprises a scent cartridge housing 221 having a slot 207 that is configured to receive a scent cartridge 209. Airflow travels through electronic lighting device 200 via an air channel 223 disposed from top end 213 to bottom end 215. It is contemplated that aperture 205 can form a first opening of air channel 223 and slot 207 can form a second opening of air channel 223. A fan 225 within outer cover 201 can be used to move the air and/or scented air through air channel 223. Thus, electronic lighting device 200 can receive air and produce scented air through air channel 223 to enhance a user's experience.

Air channel 223 can allow airflow to travel from bottom end 215 to top end 213 as shown in FIG. 2A. However, it is contemplated that in other embodiments the airflow is reversed, such that airflow travels through air channel 223 from top end 213 to bottom end 215. Regardless of the airflow, it is contemplated that air that travels in air channel 223 will contact scent cartridge 209 thereby creating scented air.

In contemplated embodiments, air channel 223 can be formed by coupling various components to one another. For example, air channel 223 can be formed by a coupling of at least two of housing 219, fan 225, and scent cartridge housing 221. In FIG. 2, housing 219 couples scent cartridge housing 221 to thereby form air channel 223 that extends through housing 219 and scent cartridge housing 221 from top end 213 to bottom end 215. Thus, FIG. 2 shows a two-part internal housing assembly (housing 219 and scent cartridge housing 221).

Housing 219 can have an arm 227 affixed to housing 219 to support movement of flame element 203 within housing 219 as shown in FIG. 2B. It is contemplated that arm 227 can be a separate component of housing 219, such that arm 227 attaches to housing 219 to thereby support flame element 203. However, in other contemplated embodiments, arm 227 is a region of housing 219, such that arm 227 and housing 219 are a single component (e.g., a single injection molded component).

Arm 227 typically extends towards the center of aperture 205 to support flame element 203. It is contemplated that flame element 203 comprises a hollow interior 229 and a projection 231 that extends into hollow interior 229. To suspend flame element 203, arm 227 can comprise a recess that is configured to receive projection 231 to thereby support flame element 203 within housing 219. In other embodiments, it is contemplated that arm 227 comprises an upward projection that rests on an apex of hollow interior 229 of flame element 203 to thereby support flame element 203 within housing 219. However, flame element 203 can be supported within or at electronic lighting device 200 using other manners without departing from the scope of the invention.

It is contemplated that various mechanisms (e.g., electromagnet, fan, etc.) can be used to generate motion of flame element 203 as described above, and such mechanisms are incorporated herein. Moreover, housing 219 can further comprise a light source 233 that is configured to emit light onto flame element 203 to create a realistic candle light effect either directly or indirectly such as through the use of a mirror, fiber optic cable, or other means.

Fan 225 is disposed within housing 219 and positioned above scent cartridge housing 221 in FIG. 2A. However, it is also contemplated that fan 225 can be positioned below scent cartridge housing 221. Fan 225 can be used to move air or scented air through air channel 223. Fan 225 can be coupled to a fan controller that is configured to vary a speed of fan 225 as a function of time. It is contemplated that the fan controller is configured to operate fan 225 at 100% speed for a first amount of time followed by 0% speed for a second amount of time and followed by 70% speed for a third amount of time to thereby maintain scent. For example, the first amount of time can be 1-15 minutes, and preferably 1-5 minutes, the second amount of time can be 1-10 minutes, and preferably 1-5 minutes, and the third amount of time can be 10 seconds to 1 minute or the remaining time that electronic lighting device 200 is on. More typically, the first amount of time can be 2-4 minutes, the second amount of time can be 2-4 minutes, and the third amount of time can be 20-40 seconds or the remaining time that electronic lighting device 200 is on. Moreover, fan 225 in the third amount of time can be operated at 10-95% speed, and more typically at 40-90% speed, and most typically at 60-80% speed.

It should be appreciated that the variable speed configuration of fan 225 advantageously dispenses scent within tolerable limits. In addition, the variable speed configuration of fan 225 provides a more efficient manner of quickly dispensing scented air, which reduces the time between turning on electronic lighting device 200 and receiving scented air. Thus, in contemplated embodiments, fan controller operates fan 225 at maximum (100%) or near maximum speed to quickly disperse scented air, and reduces the speed (<10%) or turns off fan 225 to allow for the dispersion of the scented air, and then the fan controller operates fan 225 at a variable speed to maintain a steady state level of scented air in the surrounding environment.

It is contemplated that the fan controller can also account for fluctuations of power provided by the battery of electronic lighting device 200. For example, if the battery in electronic lighting device 200 is low, then the fan controller can send additional power to fan 225 to account for the reduced power output of the battery and thereby maintain a constant speed of fan 225.

Scent cartridge housing 221 can be disposed on bottom end 215 as shown in FIG. 2A. As discussed above, scent cartridge housing 221 can comprise slot 207 for receiving scent cartridge 209. It is contemplated that scent cartridge housing 221 can comprise a battery compartment 211 that is configured to receive a battery. Thus, no separate housing is needed to receive a battery. Scent cartridge housing 221 can also comprise a leg 202 on bottom end 215 that can create a space between electronic lighting device 200 and a surface that is supports electronic lighting device 200.

As described above, FIG. 2A shows a two-part internal housing assembly (housing 219 and scent cartridge housing 221). It is contemplated that housing 219 and scent cartridge housing 221 are no more than two components. However, it is also contemplated that additional housings can form the internal structure of an electronic lighting device. It should be appreciated that there are numerous benefits to providing more housings that couple within an electronic lighting device. For example, various housing can simplify the modification of components within an electronic lighting device by allowing substitution of one component housing (e.g., a fan housing for a certain model of fan) with another component housing (e.g., a fan housing for another model of a fan). Thus, a user can simply remove the outer cover and decouple a first housing from the other housings in the electronic lighting device to substitute the first housing for a second housing.

Furthermore, it is contemplated that each of the various housings can comprise a right side and a left side, or top and bottom pieces that removably couple to form the housing. For example, it is contemplated that at least one of housing 219 and scent cartridge housing 221 can comprise a right side (e.g., a right half of housing 219 and/or a right half of scent cartridge housing 221) and a left side (e.g., a left half of housing 219 and/or a left half of scent cartridge housing 221) that removably couple to form the housing and thereby form air channel 223.

Figure 3:
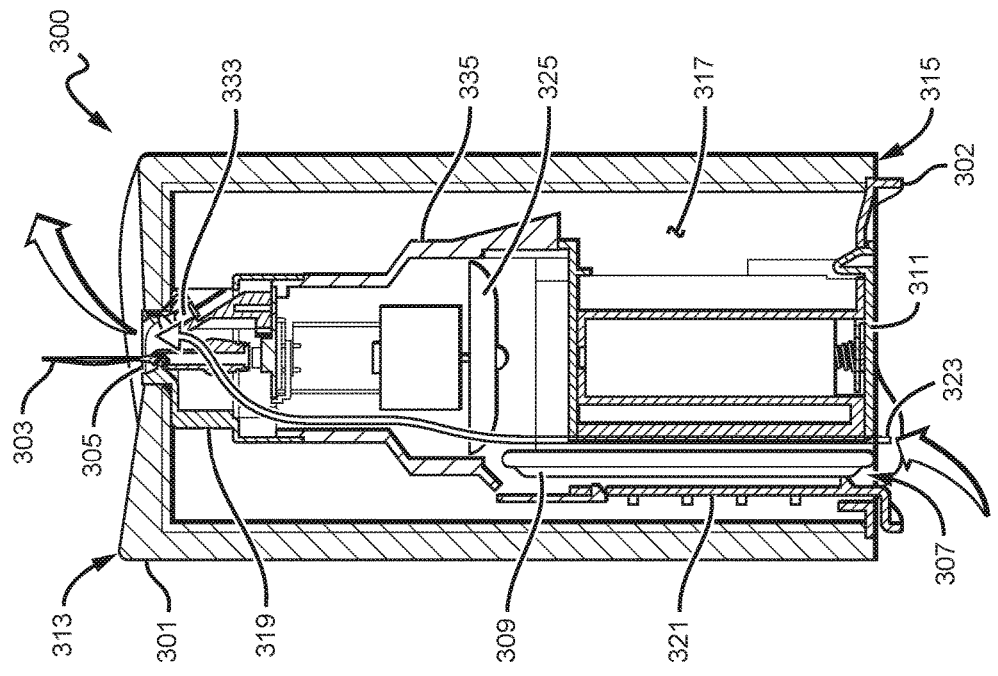
FIG. 3 is a cross-sectional view of an embodiment of an electronic lighting device.

FIG. 3 shows an electronic lighting device 300 having similar components as described in electronic lighting device 200 shown in FIG. 2A. Electronic lighting device 300 comprises an outer cover 301 having a top end 313 and a bottom end 315 that define an internal cavity 317. A housing 319 is disposed within internal cavity 317 and comprises an aperture 305. A flame element 303 extends through aperture 305 on top end 313, and is supported by housing 319 to create a realistic candle light effect. A light source 333 can be disposed on housing 319 to emit light onto flame element 303 to create an illuminating effect.

Electronic lighting device 300 further comprises a scent cartridge housing 321 that has a slot 307 configured to receive a scent cartridge 309. Scent cartridge housing 321 can comprise a battery compartment 311 configured to receive a battery. Similar to the electronic lighting devices above, airflow travels through electronic lighting device 300 via an air channel 323. A fan 325 can be used to move the air and/or scented air through air channel 323. Airflow can be from top end 313 to bottom end 315 or the reverse, and it is contemplated that electronic lighting device 300 further comprises leg 302. Thus, electronic lighting device 300 can receive air and produce scented air through air channel 323 to enhance a user's experience.

Unlike the two-part internal housing assembly shown in FIG. 2A, electronic lighting device 300 comprises a three-part internal housing assembly. As discussed above, electronic lighting device 300 comprises housing 319 and scent cartridge housing 321 that are disposed within internal cavity 317 of outer cover 301. Additionally, electronic lighting device 300 comprises a fan housing 335 that is sized and dimensioned to receive fan 325, and fan 325 can be coupled to a fan controller as described above. Typically, housing 319, scent cartridge housing 321, and fan housing 335 are separate components that can couple one another to thereby form air channel 323 through housing 319, scent cartridge housing 321, and fan housing 335 from top end 313 to bottom end 315.

Furthermore, although two-part and three-part internal housings have been described, it is contemplated that an electronic lighting device 400 can have a four-part internal housing as shown in FIG. 4. Electronic lighting device 400 comprises many of the components discussed above, including, but not limited to, an outer cover 401 having a top end 413 and a bottom end 415 that define an internal cavity 417, a housing 419 that comprises an aperture 405, a flame element 403 and a light source 433, a scent cartridge housing 421 having a slot 407 that is configured to receive a scent cartridge 409, an air channel 423 disposed from top end 413 to bottom end 415, and a fan 425, which could be coupled to a fan controller as described above, disposed within a fan housing 435.

Additionally, electronic lighting device comprises a battery compartment 411 configured to receive a battery. It should be noted that battery compartment 411 is a separate housing from housing 419, scent cartridge housing 421, and a fan housing 435 to form a four-part internal housing. Thus, housing 419, scent cartridge housing 421, fan housing 435, and battery compartment 411 couple one another to thereby form air channel 423 through electronic lighting device 400.

Electronic lighting device comprises a leg 402 disposed on bottom end 415. It is contemplated that leg 402 can be a part of at least one of battery compartment 411 and scent cartridge housing 421. Furthermore, it is contemplated that electronic lighting device comprises a plurality of legs.

As discussed above, two-part, three-part, and four-part internal housings are described for various electronic lighting devices. The internal housing forms an air channel for airflow through the various electronic lighting devices. Typically, the air channel travels through the various housings from the bottom end to the top end of electronic lighting devices or vice versa. In other words, the air channel is typically disposed within the various housing through the electronic lighting devices.

While the embodiments described above comprised different housings that couple to form the internal housing and form the air channel, a single unit housing is contemplated. Preferably, the single unit housing comprises a single, injection-molded piece having a plurality of openings or recesses configured to receive and support various components of the electronic lighting device. For example, the single, injection-molded housing can include an opening through which a PCB board can be inserted to control operation of a drive mechanism and/or light source. The housing can include a recess or opening where a LED could be placed or inserted through. Another hole could allow for insertion of a fan, or the fan could be inserted through the same hole as the PCB Board for example.

FIG. 5 shows an electronic lighting device 500 comprising a housing 519 that extends from a top end 513 to a bottom end 515. Electronic lighting device 500 further comprises an outer cover 501 having top end 513 and bottom end 515 that at least partially define an internal cavity 517. Housing 519 can be disposed within internal cavity 517. A flame element 503 extends through an aperture 505 of housing 519 and is supported by an arm of housing 519 to thereby simulate the movement of a real candle light. A slot 507 is disposed on bottom end 515 of housing 519, and slot 507 is configured to receive a scent cartridge 509. A fan 525 is disposed within housing 519 to assist in airflow via an air channel 523, wherein fan 525 can be coupled to a fan controller as described above. Air channel 523 is disposed from top end 513 to bottom end 515 and typically directs airflow from bottom end 515 to top end 513.

Housing 519 further comprises a groove 537 that is configured to receive a light source 533. As discussed above, light source 533 emits light onto flame element 503. Groove 537 is typically disposed near top end 513. It is contemplated that additional grooves can be disposed on housing 519 to accommodate for additional light sources or other components.

Additionally, housing 519 can comprise a battery compartment 511 that is configured to receive a battery. Thus, it is contemplated that housing 519 can be a single unit. In other words, no other housings (e.g., fan housing, battery compartment housing, scent cartridge housing, etc.) couple to housing 519, rather housing 519 comprises grooves and/or slots that are sized and dimensioned to receive the various components (e.g., fan, scent cartridge, battery, light source, etc.) of electronic lighting device 500. It is contemplated that housing 519 can be formed by injection molding, and more particularly, it is contemplated that housing 519 is a single injection molded piece. For example, it is contemplated that a housing and a scent cartridge housing as described above are combined into a single component (typically, injection molded), such that a single housing 519 provides the grooves and/or slots to house the various components of electronic lighting device 500.

Housing 519 can be sized and dimensioned to fit in a number of various configurations within outer cover 501. For example, it is contemplated that an outer surface of housing 519 abuts an inner surface of outer cover 501 when housing 519 is disposed within outer cover 501. It should be noted that such configurations are also applicable to other embodiments having additional housings, including, but not limited to, a scent cartridge housing and a fan housing. For example, in such embodiments having additional housings, at least one of the scent cartridge housing and the fan housing can have an outer surface that abuts an inner surface of the outer cover.

As briefly described above, it is contemplated that electronic lighting devices can comprise more than one scent cartridge. An electronic lighting device having multiple scent cartridges can provide at least one of (i) a stronger scent using two of the same or similar scent cartridges, (ii) a blended scent using two similar or distinct scent cartridges, (iii) a selection of scents from which to chose, and (iv) a backup scent cartridge by having a first scent cartridge being used and providing a second scent cartridge that remains idle until the first scent cartridge is consumed. FIG. 6A shows an electronic lighting device 600 that comprises multiple scent cartridges.

Similar to the other electronic lighting devices, electronic lighting device 600 comprises an outer cover 601 having a top end 613 and a bottom end 615 that partially define an internal cavity 617, a housing 619 disposed within internal cavity 617 having an aperture 605 and a light source 633, a flame element 603 that extends above aperture 605, a scent cartridge housing 621 that comprises a slot 607 configured to receive a scent cartridge 609, and a fan 625 that is disposed within housing 619 and is configured to provide airflow of air and scented air via an air channel 623. Fan 625 can be coupled to a fan controller as described above.

Electronic lighting device 600 further comprises a second slot 639 disposed on bottom end 615 and configured to receive a second scent cartridge 641. Second slot 639 can be disposed on a second scent cartridge housing 643. However, in other embodiments, second slot 639 can be disposed on scent cartridge housing 621, a battery compartment 611, or on housing 619. Second slot 639 and second scent cartridge housing 643 are disposed adjacent to scent cartridge housing 621 and slot 607. For example, second scent cartridge housing 643 and second slot 639 can abut scent cartridge housing 621 and slot 607. In another example, second scent cartridge housing 643 and second slot 639 can be disposed between scent cartridge housing 621 and battery compartment 611.

FIG. 6B is a bottom view of electronic lighting device 600. Slot 607 abuts second slot 639. It should be appreciated that slot 607 and second slot 639 can function as an ingress point for air into electronic lighting device 600 and/or as an exit point for air leaving electronic lighting device 600. For example, it is contemplated that aperture 605 can form a first opening of air channel 623, slot 607 can form a second opening of air channel 623, and second slot 639 can form a third opening of air channel 623. Second slot 639 is typically adjacent to a battery cover 645 of battery compartment 611. It is contemplated that having slot 607 adjacent to second slot 639 can help concentrate the scent in air channel 623 because of the close proximity of scent cartridge 609 and second scent cartridge 641.

It is also contemplated that the scent cartridge housings and/or slots for receiving a scent cartridge can be separated from one another by a distance or a component/housing, such that they are on opposite ends. For example, FIG. 7A shows an electronic lighting device comprising a slot 707 and a second slot 739 separated by a battery compartment 711. It is contemplated that slot 707 is configured to receive a scent cartridge 709, and second slot 739 is configured to receive a second scent cartridge. Electronic lighting device 700 has many of the similar components described in the other embodiments, including an outer cover 701 having a top end 713 and a bottom end 715 that partially define an internal cavity 717, a housing 719 having a light source 733, a flame element 703 that extends above an aperture 705 of housing 719, and a leg 702 disposed on bottom end 715.

Unlike many of the other embodiments, electronic lighting device 700 comprises a fan 725 disposed on bottom end 715. It is contemplated that fan 725 can be coupled to a fan controller. A scent cartridge housing 721 and a second scent cartridge housing 743 is disposed above fan 725 in a position between fan 725 and housing 719. In other embodiments, fan 725 can be positioned above at least one of scent cartridge housing 721 and second scent cartridge housing 743.

It should be appreciated that scent cartridge housing 721 comprises a slot 707 and second scent cartridge housing 743 comprises a second slot 739. As discussed above, slot 707 and second slot 739 can be an ingress or exit point. For example, it is contemplated that aperture 705 can form a first opening of air channel 723, slot 707 can form a second opening of air channel 723, and second slot 739 can form a third opening of air channel 723.

Slot 707 and second slot 739 can be disposed on opposite ends of bottom end 715 to thereby create split air channel 723 and later combines air channel 723 within housing 719. It is contemplated that separating the scent cartridges and the slots can help reduce the intensity of the scent and/or provide less mixing between two different scent cartridges when desired. FIG. 7B shows slot 707 separated from second slot 739 by a cover 745 on bottom end 715.

Many different sized and shaped scent cartridges can be used in the various embodiments described herein. FIG. 8A shows an exemplary scent cartridge 809 having a rectangular shape. However, scent cartridge 809 can be many other shapes to be received by slot, including circular, curved, triangular, pentagonal, octagonal, and so forth. Scent cartridge 809 can comprise various components that couple together to form scent cartridge 809 as shown in FIG. 8B. Scent cartridge 809 can comprise an upper frame 847 and a lower frame 855 that hold a scent pack 849. It is contemplated that upper frame 847 and lower frame 855 snap together along the perimeter of scent pack 849 as can be seen in more detail in FIG. 8C. Scent pack 849 can be initially covered by removable cover 851 (e.g., an aluminum foil or other material) that can be peeled off to allow the fragrance/scent to escape scent pack 849. To ease the process of removing removable cover 851, it is contemplated that a pull tab 853 can be used.

Preferred embodiments of scent pack 849 have a large flat surface area for air to come into contact with as it passes through an air channel within an electronic lighting device. To maximize the surface area of scent pack 849 that comes into contact with air, scent pack 849 can additionally include textured features. Including textures on scent pack 849 increases the amount of surface area open to air, thus increasing the ability of scent pack 849 to diffuse scent and the electronic lighting device's ability to distribute scented air.

It is further contemplated that scent cartridge 809 can comprise a machine-readable tag, which can include a barcode (e.g., barcode or QR code), a wireless signal (e.g., RFID tag), an electrical connection such as that used with printer cartridges, and a physical tag comprising a set of peaks and/or valleys on the cartridge that indicate the authenticity or model/type of cartridge inserted. In such embodiments, the electronic lighting device can further comprise a reader to read the machine-readable tag to execute a function or command via a controller. For example, the reader can read the machine-readable tag to thereby cause the controller to modify a color of light from a light source of the electronic lighting device or modify a speed of the fan to align with a dissipation rate of the cartridge inserted. In another example, the reader can read the machine-readable tag to thereby cause the controller to modify the fan speed settings of the fan. In yet another example, the reader can read the machine-readable tag to thereby cause the controller to modify the movement of the flame element. It is also contemplated that scent cartridge 809 having a machine-readable tag can be inserted into the electronic lighting device to override a function or command from the machine-readable tag of a previously inserted scent cartridge.

Additionally, it is contemplated that the machine-readable tag on scent cartridge 809 can be used for identification purposes to identify the type of scent cartridge 809 being used. For example, it is contemplated that an electronic lighting device can comprise a display that can be used to present the type of scent cartridge 809, which can be information on the size and aroma type. Additionally, or alternatively, the machine-readable tag of scent cartridge 809 can require a certain type or brand of electronic lighting devices. For example, the machine-readable tag of scent cartridge 809 can have authentication information that allows scent cartridge 809 to operate with a specific type or brand of electronic lighting devices. If the electronic lighting device fails to recognize the authentication of the machine-readable tag, then electronic lighting device will not function to dispense aroma from scent cartridge 809.

Scent cartridge 809 can be refilled to provide additional scent. When using a solid scent pack 849, scent cartridge 809 can be removed from the electronic lighting device and opened to replace an old scent pack 849 with a new scent pack 849. When using a liquid or gel scent to produce the aroma, it is contemplated that scent cartridge 809 comprises a chamber to store the liquid or gel scent and a slot to refill the chamber. In such embodiment, it is contemplated that scent cartridge 809 can remain in the electronic lighting device while scent cartridge 809 is being refilled, such that a dispenser can be used to couple the slot of the chamber to refill the liquid scent.

It is contemplated that scent cartridge 809 can comprise a nozzle configured to receive liquid or gel scent to refill scent cartridge 809. For example, a dispenser comprising liquid or gel scent can couple to the nozzle and dispense liquid or gel scent into scent cartridge 809. It should be appreciated that an indicator can be disposed on the dispenser and/or scent cartridge 809 that shows a user a liquid and/or gel level of the liquid or gel scent in scent cartridge 809. The nozzle can comprise a removable cap to prevent leaking of the liquid or gel scent from scent cartridge 809.

It is also contemplated that scent cartridge 809 can have a plurality of chambers to house a plurality of scent packs or liquid scents. In such embodiment, the electronic lighting device can dispense aroma from the scent pack or liquid scent in a first chamber, and then switch to dispense aroma from a second scent pack or second liquid scent in a second chamber once the scent pack or liquid scent in the first chamber is consumed. The plurality of chambers for the scent packs or liquid scents can be disposed along the perimeter of scent cartridge 809, and scent cartridge can be rotated 809 to position a second chamber in an area proximal to the air channel and/or an actuator can be used to puncture a second chamber to dispense aroma from the scent pack or liquid scent. For example, scent cartridge 809 can have a round shape having a plurality of chambers disposed on the circumference of scent cartridge 809, and scent cartridge can be used to dispense aroma from a first chamber to aroma from a second chamber. It should be appreciated that the chambers can house different scents, such that a user can select a scent type on the electronic lighting device or a remote device to switch one chamber having one scent to a second chamber having a different scent.

It is contemplated that scent cartridge 809 can be double-sided to thereby comprise a first scent pack on one side and a second scent pack on the opposite side of a single scent cartridge 809. The first and second scent packs can comprise the same or different scents. It is contemplated that each of the scent packs can comprise a pull tab. Thus, it should be appreciated that the surface area that comes into contact with air can be doubled to thereby provide a unique scent of at least two dissimilar scent packs or enhance the scent produced by a scent pack by doubling the surface area that comes into contact with air.

Figure 16A:
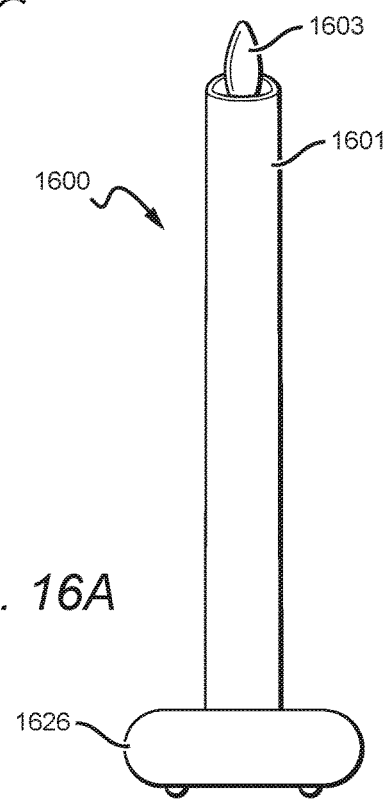
FIGS. 16A and 16B are a side view and a cross-sectional view of an embodiment of an electronic lighting device.
Figures 16B, 17A:
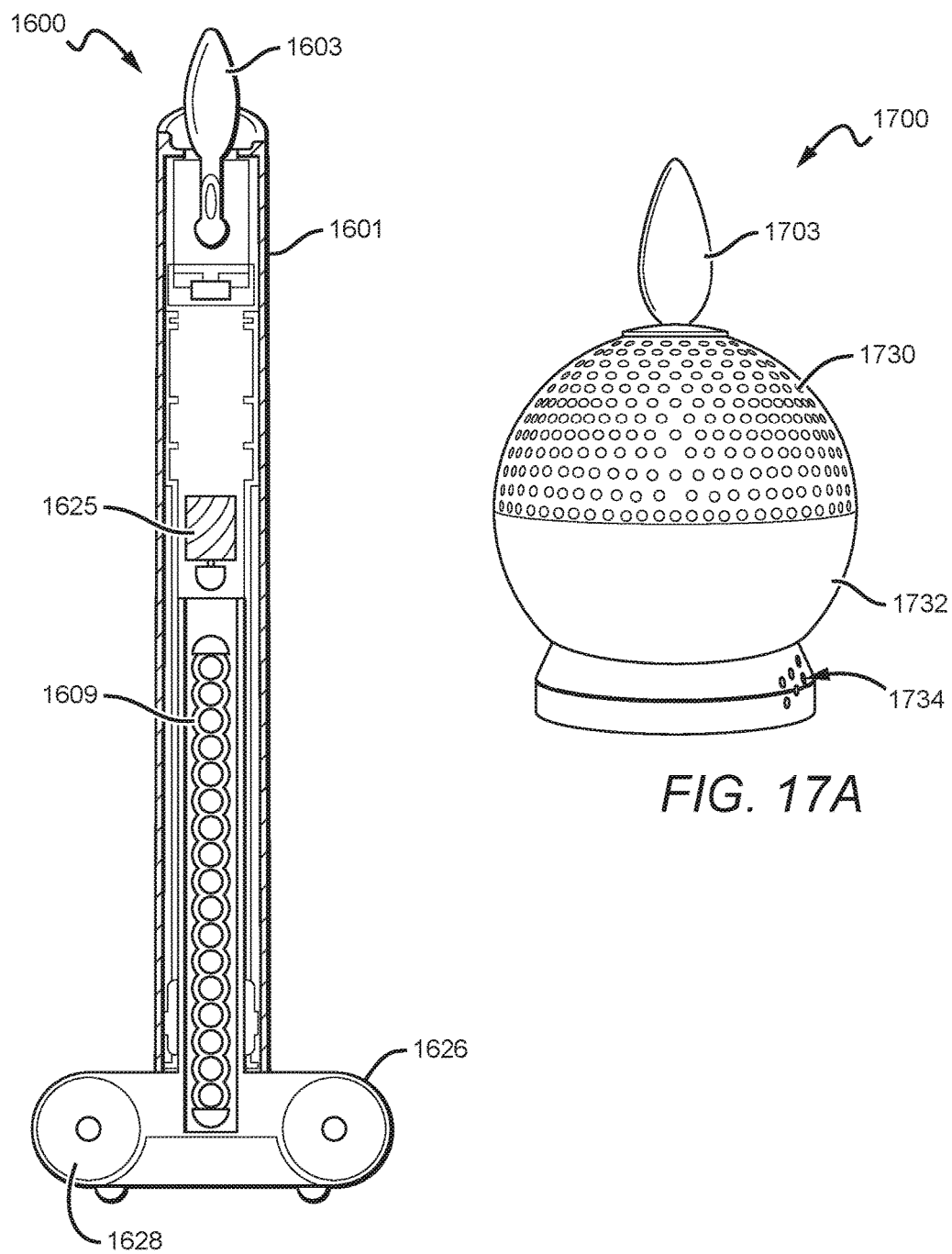
FIGS. 17A and 17B are a side view and a cross-sectional view of an embodiment of an electronic lighting device.
Figure 19A:
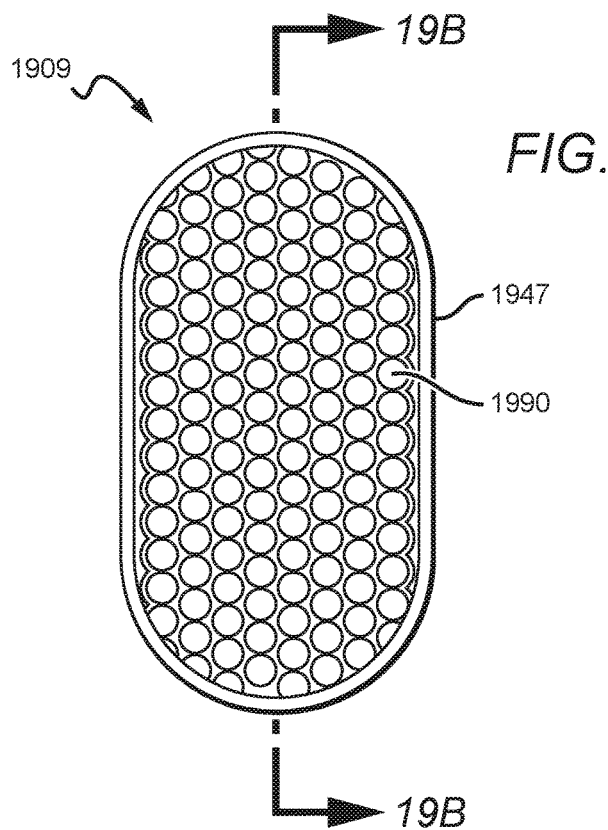
FIGS. 19A-19B are front and side views, respectively, of one embodiment of a scent cartridge.
Figure 19B:
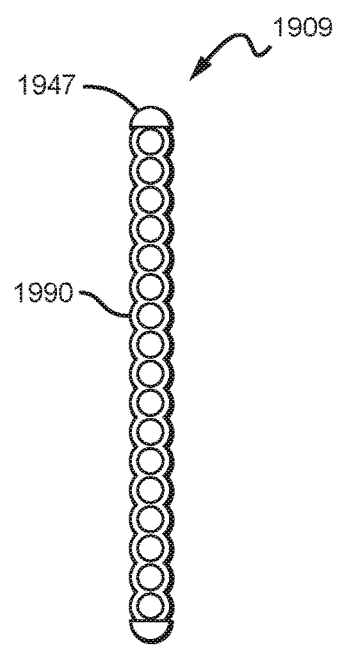

Additionally, or alternatively, it is contemplated that scent cartridge 809 can comprise a plurality of scent beads as shown in FIGS. 16B and 19A-19B. For example, a scent pack 849 can house a plurality of scent beads that are configured to release a scent. In some embodiments, each of the scent beads in scent cartridge 809 can be configured to produce the same scent. However, it is contemplated that at least two of the scent beads in scent cartridge 809 are configured to produce different scents. As another example shown in FIGS. 19A-19B, scent cartridge 1909 can include a plurality of scent beads or spheres 1990 disposed within a housing 1947 that effectively increase a surface area of the gel exposed to air, while also allowing airflow through the scent cartridge 1909. This advantageously permits the scent cartridge to be placed in a normal or parallel position with respect to a central axis of the fan.

Figure 9A:
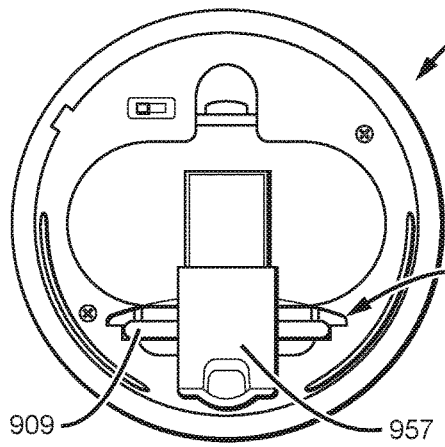
FIGS. 9A and 9B are bottom views of an embodiment of an electronic lighting device having a slide door.
Figure 9B:
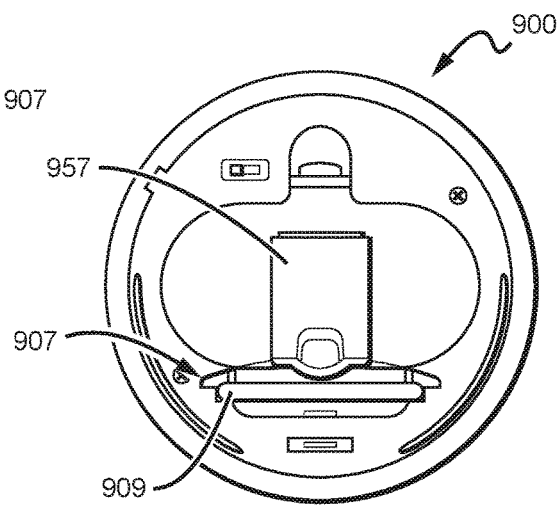

There are a number of suitable ways that scent cartridges can be held within electronic lighting devices, including but not limited to a slide door, a flap door, and a pivot lock. For example, FIGS. 9A-9B show an electronic lighting device 900 having a scent cartridge 909 within a slot 907. Scent cartridge 909 is secured in electronic lighting device using a slide door 957. Slide door 957 is shown in its closed position in FIG. 9A and in its open position in FIG. 9B. As shown in its closed position, slide door 957 blocks scent cartridge 909 from being removed from slot 907.

Figure 10A:
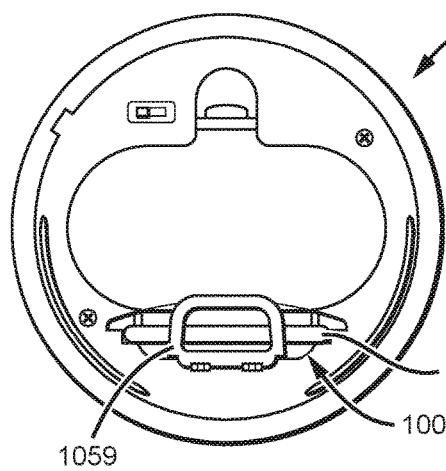
FIGS. 10A and 10B are bottom views of an embodiment of an electronic lighting device having a flap door.
Figure 10B:
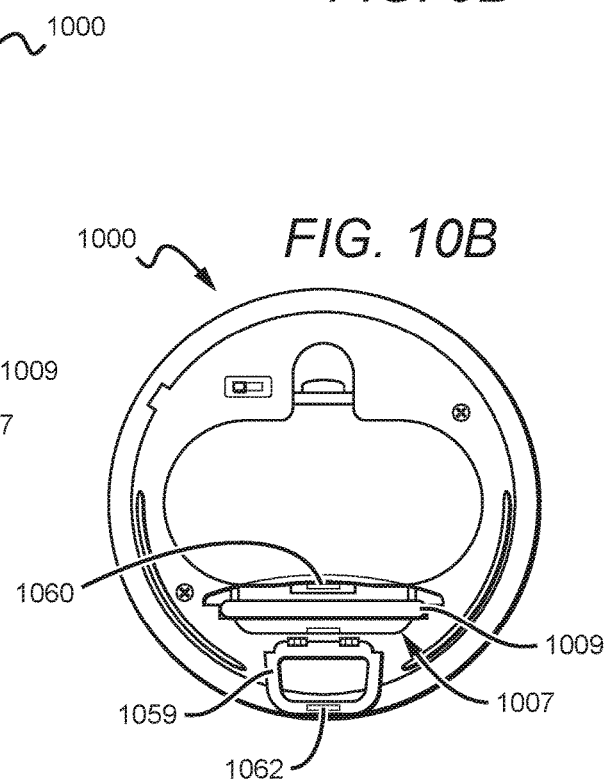

In another example, an electronic lighting device 1000 having a flap door 1059 to secure a scent cartridge 1009 in a slot 1007 as shown in FIGS. 10A-10B. Flap door 1059 has an aperture, such that scent cartridge 1009 is visible in either an open or closed position. It should be appreciated that a user can easily identify the type of scent cartridge 1009 without the need of opening flap door 1059 because scent cartridge 1009 is visible in either an open or closed position. Additionally, it should be noted flap door 1059 minimally obstructs slot 1007 to thereby provide a sufficient opening for air to enter or exit while securing scent cartridge 1009 within slot 1007.

Flap door 1059 is shown in a closed position in FIG. 10A and an open position in FIG. 10B. In its closed position, flap door 1059 obstructs scent cartridge 1009 from being removed from slot 1007. Furthermore, electronic lighting device 1000 can further comprise a catch 1060 that is sized and dimensioned to receive a projection 1062. It should be appreciated that catch 1060 and projection 1062 can comprise a press-fit or friction-fit to further secure scent cartridge 1009 in slot 1007.

Figure 11A:
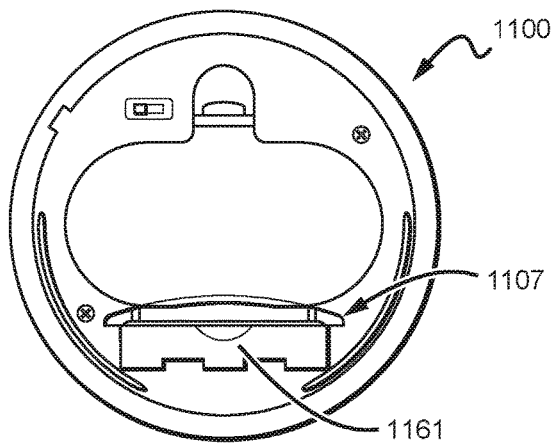
FIGS. 11A and 11B are bottom views of an embodiment of an electronic lighting device having a flap door.
Figure 11B:
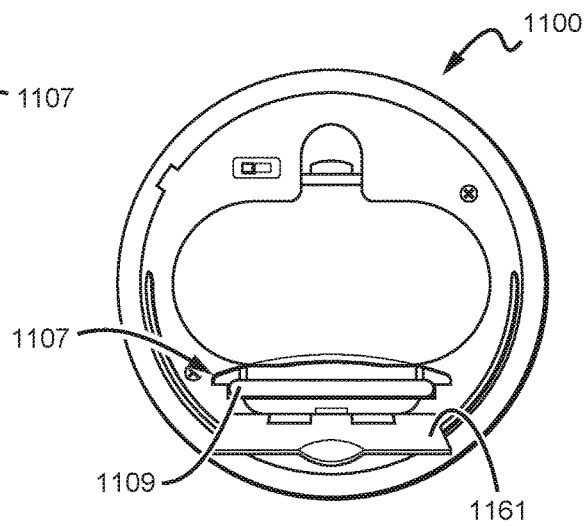

Another example of a flap door is shown in FIGS. 11A-11B. Electronic lighting device 1100 comprises a slot 1107 comprising a scent cartridge 1109. A flap door 1161 can be used to secure scent cartridge 1109 within slot 1107. FIG. 11A shows flap door 1161 in a closed position. It should be noted that scent cartridge 1109 is entirely hidden when flap door 1161 is closed. FIG. 11B shows flap door 1161 in an open position.

Figure 12A:
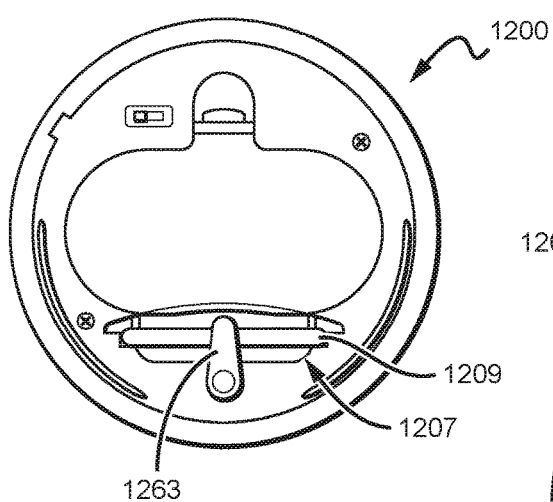
FIGS. 12A and 12B are bottom views of an embodiment of an electronic lighting device having a pivot lock.
Figure 12B:
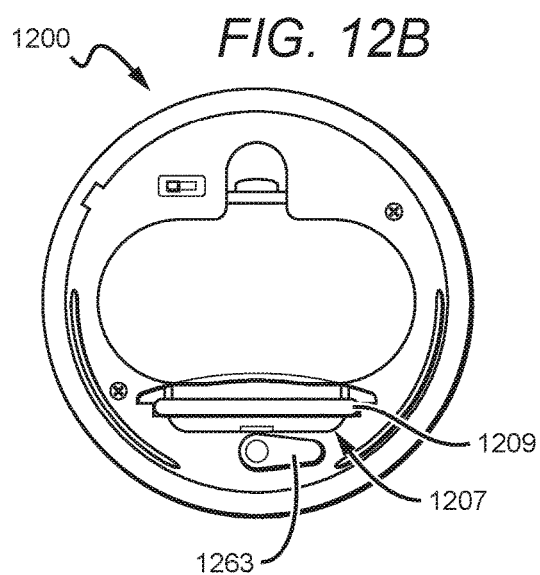

A scent cartridge 1209 can also be secured using a pivot lock 1263 as shown in FIGS. 12A-12B. An electronic lighting device 1200 can have pivot lock 1263 which is twisted to a closed position as shown in FIG. 12A or a closed position as shown in FIG. 12B. It is contemplated that pivot lock 1263 minimally obstructs slot 1207 to thereby provide a sufficient opening for air to enter or exit.

Figure 13:
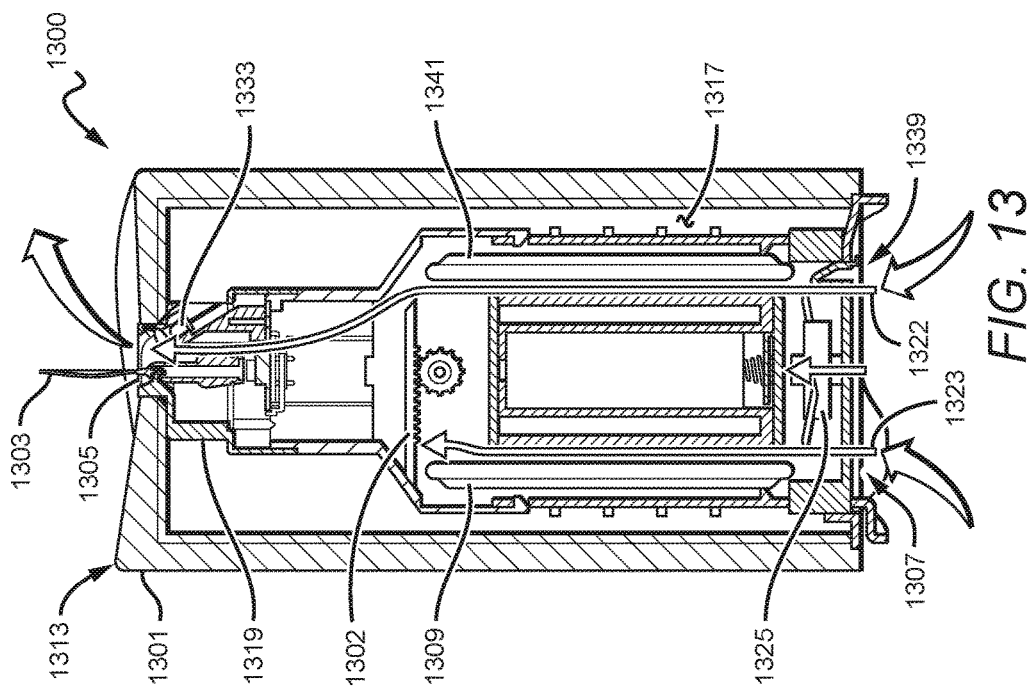
FIG. 13 is a cross-sectional view of an embodiment of an electronic lighting device.

As described above, it is contemplated that two scent cartridges can be disposed within an electronic lighting device. Advantageously, scents from different cartridges within an electronic lighting device can be combined to create new scents. In some instances, it may be desirable to block, or partially obstruct/reduce, the flow of scent from one of two or more scent cartridges in an electronic lighting device. For example, an electronic lighting device 1300 can have a door or gate 1302 that is configured to block, or partially obstruct, a flow path within electronic lighting device 1300 as shown in FIG. 13.

Electronic lighting device 1300 comprises a slot 1307 and a second slot 1339 on a bottom surface of electronic lighting device 1300. An aperture 1305 is disposed on a top end 1313 and it is contemplated that a first air channel 1323 and a second air channel 1322 extends from the bottom to top end 1313 of electronic lighting device 100. Electronic lighting device has many of the similar components described in the other embodiments, including an outer cover 1301 that defines an internal cavity 1317, a flame element 1303, a housing 1319 having a light source 1333, a scent cartridge 1309, a second scent cartridge 1341, and a fan 1325. It is contemplated that air can flow through first air channel 1323 and second air channel 1322 of electronic lighting device 1300 from a bottom end to a top end, or from a top end to a bottom end using fan 1325.

Unlike many of the other embodiments, electronic lighting device 100 has door 1302 that can be used to block or reduce an opening of at least one of first air channel 1323 and second air channel 1322. As shown in FIG. 13, door 1302 can be disposed within housing 1319 and positioned to block first air channel 1323, which allows only second air channel 1322 to extend through electronic lighting device 1300. It is contemplated that door 1302 can be positioned on the opposite side of housing 1319 to block second air channel 1322, which allows only first air channel 1323 to extend through electronic lighting device 1300, or door 1302 can be positioned in a location between first air channel 1323 and second air channel 1322 to partially block first air channel 1323 and second air channel 1322. It should be appreciated that door 1302 can be incorporated in any other embodiment to block an air channel. By blocking the air channel, it is contemplated that the scent cartridge can effectively be sealed within the channel such that little and preferably no scent may escape.

It should be appreciated that door 1302 can comprise a motorized mechanism (e.g., a rotatable gear coupled to teeth on door 1302) or some other actuator that allows door 1302 to move from one end to another end of housing 1319. It is contemplated that door 1302 can move from its current position based on a programmable timer and/or a controller that makes adjustments based on a scent received by a sensor in or adjacent to electronic lighting device 1300. Additionally, or alternatively, door 1302 can be controlled wirelessly whereby a remote control can send a signal to an actuator to move door 1302.

Figure 14A:
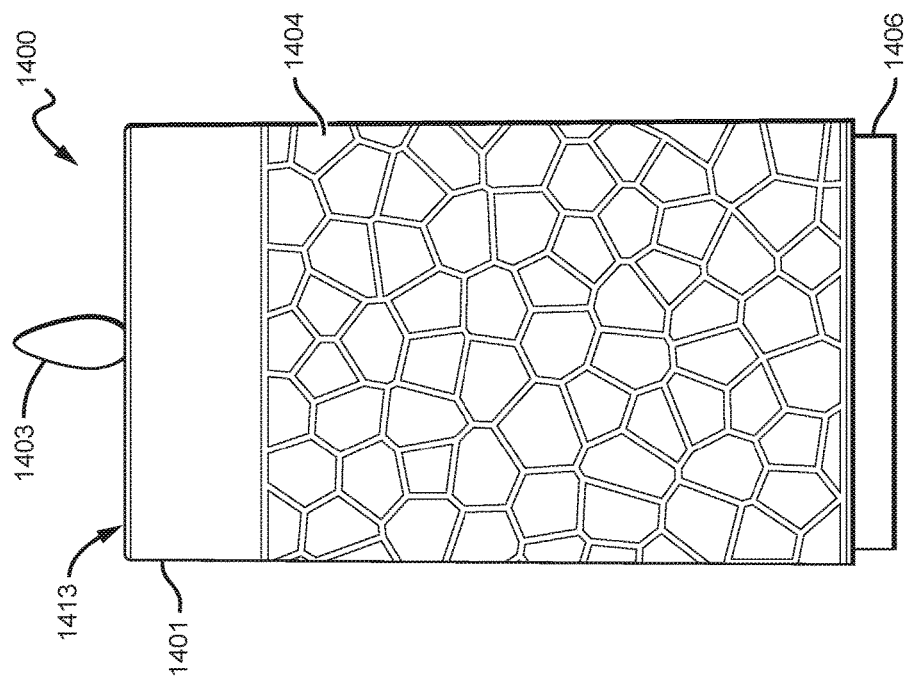
FIGS. 14A and 14B are a side view and a cross-sectional view of an embodiment of an electronic lighting device.
Figure 14B:
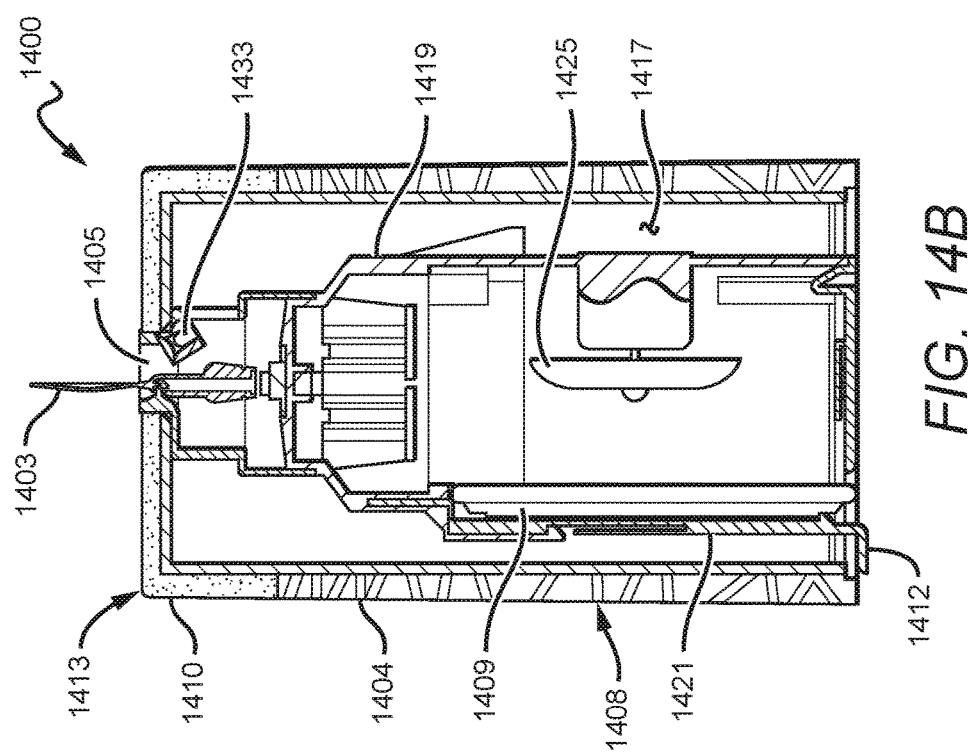

While many of the embodiments described thus far describe air flow paths that travel from the bottom to the top, or top to the bottom of an electronic lighting device, it is contemplated that an electronic lighting device 1400 can have a vented base 1404 to provide a flow path from one sidewall to another sidewall as shown in FIGS. 14A-14B. Electronic lighting device 1400 has many similar components described in the other embodiments, including a flame element 1403 that extends above an aperture 1405 of housing 1419, an internal cavity 1417, a scent cartridge 1409, a light source 1433, and a fan 1425.

Electronic lighting device 1400 comprises an extended base 1406 that is disposed below vented base 1404. It is contemplated that extended base 1406 is electronically coupled to a power switch and/or to a battery compartment, such that pushing down on a top end 1413 causes extended base 1406 to be inserted into internal cavity 1417 to complete an electrical circuit that provides power to electronic lighting device 1400. For example, when powered off, extended base 1406 can extend below vented base 1404 as shown in FIG. 14A, but extended base 1406 can be inserted, or slid, into internal cavity 1417 when top end 1413 is pushed downward as shown in FIG. 14B to power on electronic lighting device 1400.

Vented base 1404 can comprise a plurality of vents 1408 that allow air to travel through electronic lighting device 1400 (i.e., from side to side). It is contemplated that fan 1425 can be directed towards vented base 1404 to direct air from one end of vented base 1404 to an opposite end of vented base 1404. For example, the fan blades of fan 1425 can be parallel, or substantially parallel, to a wall of housing 1419 as shown in FIG. 14B. Additionally, or alternatively, fan 1425 can be positioned to face scent cartridge 1409 to guide air directly to scent cartridge 1409 as shown in FIG. 14B.

A top 1410 and vented base 1404 can couple to create internal cavity 1417. In some embodiments, top 1410 can comprise a waxy surface to create an appearance of a real candle. It is contemplated that top 1410 and vented base 1404 can be a single piece.

Scent cartridge 1409 can be housed in a scent cartridge housing 1421. When disposed inside internal cavity 1417 and housing 1419, scent cartridge 1409 is positioned in front of fan 1425. It is contemplated that scent cartridge housing 1421 and scent cartridge 1409 can be removed from internal cavity 1417 and housing 1419 by pulling downward on handle 1412. For example, scent cartridge 1409 and scent cartridge housing 1421 can be slid out of housing 1419 and internal cavity 1417. When outside internal cavity 1417, scent cartridge 1409 can be removed and replaced with another scent cartridge, and the scent cartridge housing 1421 with the new scent cartridge can be slid into internal cavity 1417 and housing 1419.

In other contemplated embodiments, it is contemplated that the scent cartridge housing 1421 can include a slidable carrier that is configured to slide into and out from the device 1400. One or more scent cartridges can be positioned on the carrier and inserted into the housing 1421 by sliding the carrier into the device 1400.

It is further contemplated that the entire device 1400 can be pushed down to turn the device 1400 on and off. For example, the device 1400 can include feet that can be inserted into the housing when the device 1400 is pushed in a downwardly direction. A spring positioned adjacent the feet can be used to cause the feet to exit the housing when the downward force is removed. In this manner, control of the candle can be accomplished by a user simply pushing the candle in a downward direction.

Figure 15A:
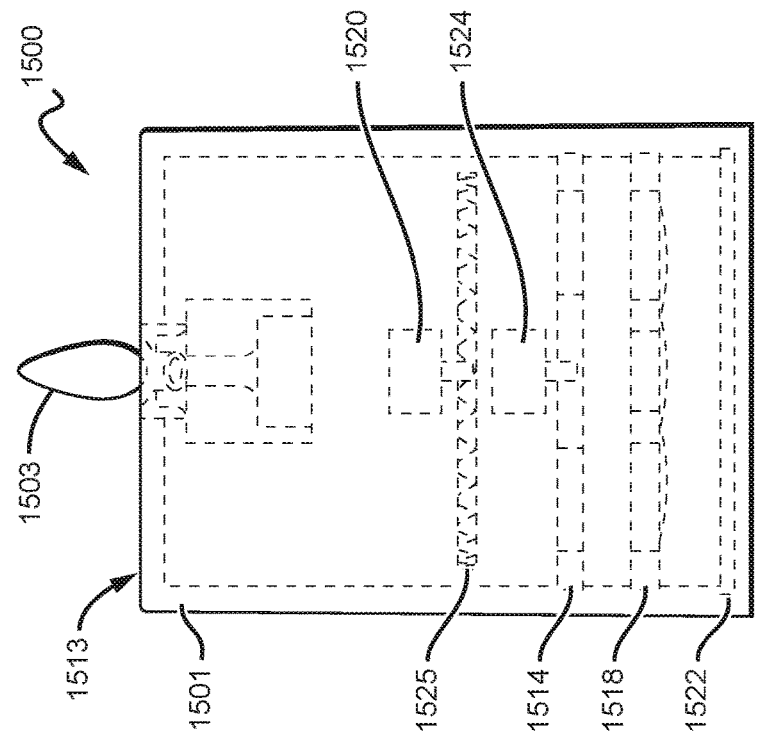
FIGS. 15A and 15B are a cross-sectional view and an exploded view of an embodiment of an electronic lighting device.

As discussed above, it may be desirable to block, or reduce, a scent from one scent cartridge when more than one scent cartridge is disposed within an electronic lighting device. As shown in FIG. 13, a door can be used to block air from one of two scented cartridges. In another embodiment, it is contemplated that an electronic lighting device 1500 can comprise a plate 1514 having an aperture 1516 and a rotatable scent plate 1518 holding a plurality of scent cartridges 1509 as shown in FIGS. 15A-15B whereby the scent dispensed by electronic lighting device 1500 is primarily from the scent cartridge that is aligned with aperture 1516.

Electronic lighting device comprises a fan 1525 coupled to a fan motor 1520. Typically, fan 1525 spins in a direction that promotes air movement from a bottom to a top of electronic lighting device 1500. However, it is contemplated that fan 1525 can be spun in a direction that promotes air movement from a top to a bottom of electronic lighting device 1500. Air can flow through a vented base 1522 having a plurality of vents disposed on the bottom of electronic lighting device 1500. Additionally, or alternatively, vented base 1522 can comprise a charging port for charging a rechargeable battery of electronic lighting device 1500.

Plate 1514 can also comprise a plate motor 1524 that can rotate plate 1514 to align aperture 1516 with a scent cartridge on scent plate 1518. It is contemplated at least one of plate 1514 and scent plate 1518 are rotatable. For example, plate 1514 can be rotatable and scent plate 1518 can be stationary, such that plate 1514 rotates to align aperture 1516 with the appropriate scent cartridge on scent plate 1518. In another example, plate 1514 can be stationary and scent plate 1518 can be rotatable, such that scent plate 1518 rotates to align the appropriate scent cartridge with aperture 1516. It is contemplated that at least one of plate 1514 and scent plate 1518 can be wirelessly controlled. Additionally, or alternatively, the movement of at least one of plate 1514 and scent plate 1518 can be based on a programmable timer that rotates at least one of plate 1514 and scent plate 1518 on pre-determined time intervals.

Figure 15B:
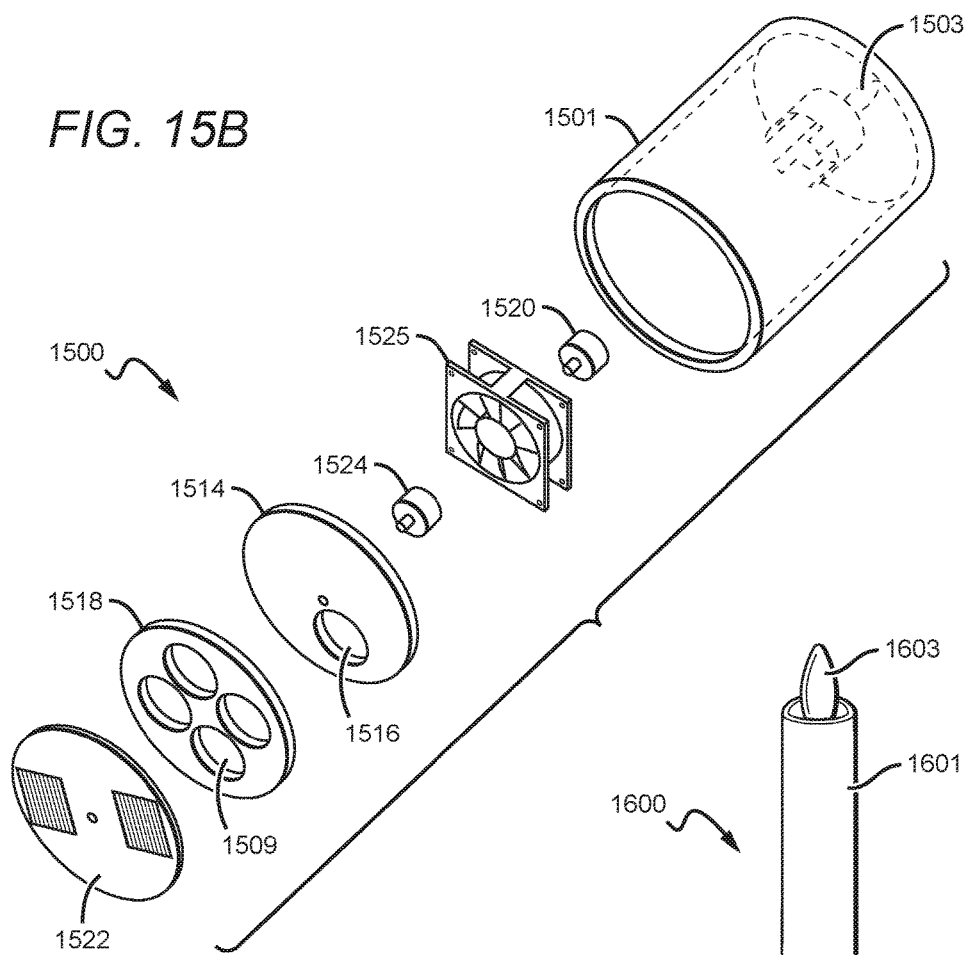

Scent plate 1518 comprises four slots that house the plurality of scent cartridges 1509 as shown in FIG. 15B. However, it is contemplated that scent plate 1518 can have any number of slots to hold a scent cartridge or a plurality of scent cartridges 1509. Additionally, or alternatively, slots on scent plate 1518 and aperture 1516 on plate 1514 can be the same shape or different shapes. It is contemplated that scent plate 1518 can house a plurality of scent gels that can be rotated to align with aperture 1516 as desired by a user.

It should be appreciated that electronic lighting devices can come in different shapes. For example, electronic lighting device 1600 can have an elongated outer cover 1601 that mimics a taper candle as shown in FIGS. 16A-16B. Similar to the other embodiments, electronic lighting device 1600 comprises a flame element 1603 that extends from a top of outer cover 1601, and a fan 1625 that is used to guide air through electronic lighting device 1600.

Electronic lighting device 1600 comprises a scent cartridge 1609. It is contemplated that scent cartridge 1609 can comprise a plurality of scented beads that increase a surface area of scent material exposed to the air. At the bottom of electronic lighting device 1600 is a base 1626. It is contemplated that base 1626 can house a rechargeable battery 1628 and comprise a charging port on its bottom surface. However, in other embodiments, base 1626 can house a disposable battery.

Figure 17B:
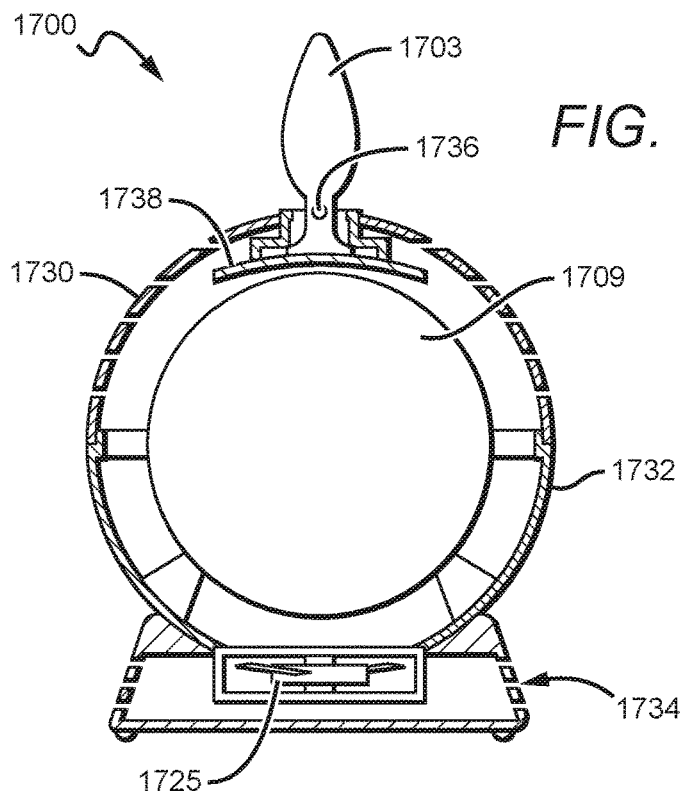

In another example, electronic lighting device 1700 can have a circular shape as shown in FIGS. 17A-17B. Electronic lighting device 1700 comprises a vented top 1730 and a base 1732. Vented top 1730 can removably couple base 1732 to insert or remove a scent cartridge 1709. It should be appreciated that scent cartridge 1709 can be refillable. For example, scent cartridge 1709 can be at least one of a gel-filled sphere and a scent bead filled sphere.

Base 1732 can comprise a plurality of vents 1734. The combination of vented top 1730 and plurality of vents 1734 provide various options for air flow through electronic lighting device 1700. It is contemplated that fan 1725 can be used to guide air through electronic lighting device 1700.

Flame element 1703 can comprise a light source 1736. Light source 1736 can be electronically controlled using a circuit board 1738. It is contemplated that circuit board 1738 can control light source 1735 so that it mimics a real candle light.

Figure 18:
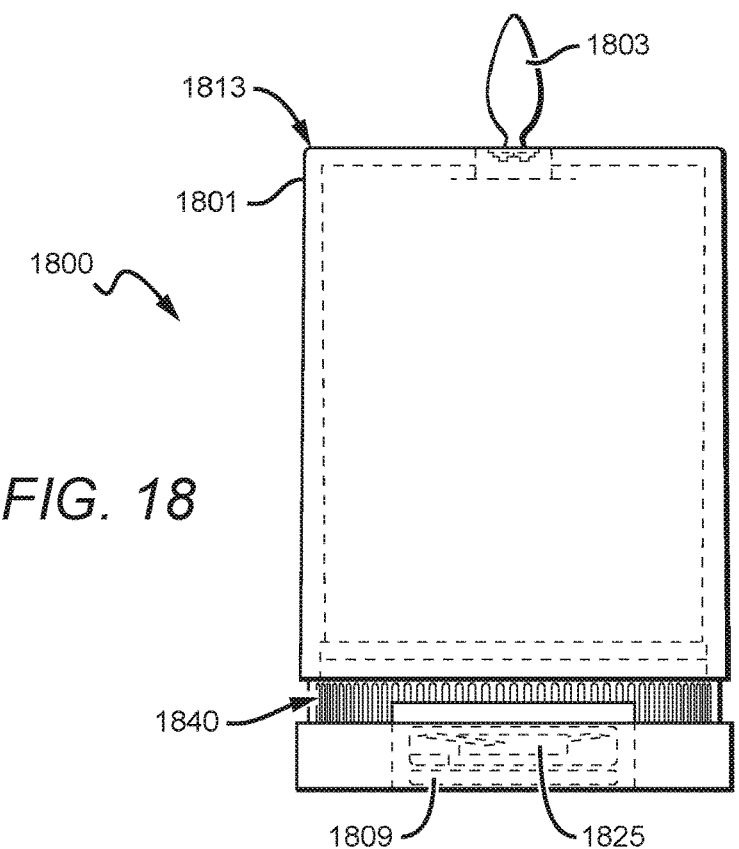
FIG. 18 is a partial cross-sectional view of an embodiment of an electronic lighting device.

While many of the embodiments described a scent cartridge positioned within an internal cavity of an electronic lighting device, it is contemplated that a scent cartridge can alternatively be disposed outside the internal cavity. For example, in FIG. 18, electronic lighting device 1800 comprises a scent cartridge 1809 that is disposed on the bottom of electronic lighting device 1800. Electronic lighting device 1800 has many similar components described in other embodiments, including an outer cover 1801 having a top end 1813 and a bottom end, a flame element 1803 that is disposed above a top end 1813, and a fan 1825.

Electronic lighting device 1800 further comprises a plurality of vents 1840 that allow for air flow from a bottom of the device outwardly through the sides of the vents or mesh base. It is contemplated that air can flow through scent cartridge 1809 and exit through plurality of vents 1840 to provide a scent. Alternatively, it is contemplated that plurality of vents 1840 can be disposed below or can surround scent cartridge 1809, such that air is directed from an internal cavity of electronic lighting device to a plurality of vents 1840 disposed below or surrounding scent cartridge 1809.

It is contemplated that any two of the electronic lighting devices described above can interact with one another. In one embodiment, a first electronic lighting device can communicate with a second electronic lighting device to coordinate a function or command of the electronic lighting devices. For example, the first electronic lighting device can communicate with the second electronic lighting device to coordinate a color to use on the flame element (e.g., the first electronic lighting device uses a green color and the second electronic lighting device uses a blue color, etc.).

Additionally, or alternatively, the first electronic lighting device can communicate with the second electronic device to share a status that the second electronic lighting device can use to execute a function or command. For example, the first electronic lighting device can communicate with the second electronic lighting device to share a status of empty scent cartridge, which the second electronic lighting device can use to provide additional power to the fan to make up for the lack of aroma from the first electronic lighting device.

The first electronic lighting device and the second electronic lighting device can communicate in many suitable ways. For example, the first and second electronic lighting devices can have wireless communication (e.g., Bluetooth, WiFi/internet, etc.) or wired communication (e.g., USB cable, Ethernet cable, optical fiber cable, etc.).

In other contemplated embodiments, a scent cartridge can snap into place by pushing it into the slot until the scent cartridge latches into place, and the scent cartridge can be removed by pressing the scent cartridge inward until it clicks again to release the latch.

Although scent cartridges are described in many of the embodiments described above, it should be appreciated that scent cartridges can be replaced with bug repellant cartridges or other types of cartridges that emit gas or a scent. For example, an electronic lighting device can comprise a bug repellant cartridge to provide protection from bug (e.g., mosquito, ticks, gnats, biting flies, etc.) bites. It is also contemplated that any of the electronic lighting devices can comprise a solar panel to provide power to the electronic lighting device.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Accordingly, in some embodiments, the numerical parameters set forth in the written description and attached claims are approximations that can vary depending upon the desired properties sought to be obtained by a particular embodiment. Notwithstanding that the numerical ranges and parameters setting forth the broad scope of some embodiments of the invention are approximations, the numerical values set forth in the specific examples are reported as precisely as practicable. Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. An electronic lighting device, comprising:
   an outer cover having a top end and a bottom end that at least partially define an internal cavity;
   a housing disposed within the internal cavity at the top end, wherein the housing comprises an aperture;
   a flame element that extends through the aperture and is supported by the housing;
   a fan disposed within the outer cover;
   a fan controller electrically coupled with the fan, and configured to vary a speed of the fan as a function of time, wherein the fan controller is programmed to automatically operate the fan at full speed when the fan is first powered on for a predetermined time period, then reduce the fan speed to less than 20% of the full speed for a second predetermined time period, and then increase the fan speed to between 50-80% of the full speed for a third predetermined time period;
   a scent cartridge housing comprising a slot configured to receive a scent cartridge; and
   an air channel disposed from the top end to the bottom end and configured to direct airflow from the bottom end to the top end, wherein the air channel is formed by coupling the housing and the scent cartridge housing;
   feet extending from a bottom surface of the housing, wherein the feet are configured to slide inwardly from a first position to a second position when a downward force is applied to the housing, and wherein movement of the feet to the second position causes the fan to power on or off.

2. The electronic lighting device of claim 1, wherein the housing comprises an arm affixed to the housing that supports movement of the flame element within the housing.

3. The electronic lighting device of claim 2, wherein the flame element comprises a hollow interior and a projection that extends into the hollow interior, and wherein the arm comprises a recess that is configured to receive the projection to thereby support the flame element within the housing.

4. The electronic lighting device of claim 1, wherein the fan controller is further programmed to reduce the fan speed to 0% of the full speed after the predetermined time period where the fan operates at full speed.

5. The electronic lighting device of claim 1, wherein the first predetermined time period is between 1-5 minutes.

6. The electronic lighting device of claim 1, wherein the scent cartridge housing further comprises a slide door, a flap door, or a pivot lock configured to secure the scent cartridge within the slot.

7. The electronic lighting device of claim 1, further comprising:

a second scent cartridge housing comprising a second slot configured to receive a second scent cartridge, wherein the second scent cartridge housing is disposed between the fan and the housing; and a movable door that is configured to selectively close the first or second scent cartridge housing from the air channel.

8. The electronic lighting device of claim 1, further comprising an electromagnet coil disposed within the housing that is configured to generate an electromagnetic field that interacts with a ferrous material or a magnet disposed on the flame element to cause movement to the flame element.

9. The electronic lighting device of claim 1, wherein the fan controller is further configured to increase power to the fan as a function of a power level of a battery disposed within a battery compartment of the housing.

10. An electronic lighting device, comprising:
an outer cover having a top end and a bottom end that at least partially define an internal cavity;
a housing disposed within the internal cavity at the top end, wherein the housing comprises an aperture;
a fan disposed within the outer cover;
first and second slots disposed on the bottom end that are each configured to receive a distinct scent cartridge;
an air channel disposed from the top end to the bottom end, wherein the first and second slots form first and second openings, respectively of the air channel and the aperture forms a third opening of the air channel; and
a movable door configured to selectively obstruct a path of air from the first slot to the air channel or the second slot to the air channel, wherein the door obstructs the path of air from the first slot to the air channel when in a first position and obstructs the path of air from the second slot to the air channel when in a second position;
a scent cartridge housing comprising the slot, wherein the housing and the scent cartridge housing are no more than two components, wherein the housing and the scent cartridge housing comprise a single, injection-molded piece having a plurality of openings or recesses, each of which is configured to receive a component of the device, wherein the component comprises a light source, a fan, or a PCB board.

11. The electronic lighting device of claim 10, further comprising a second air channel disposed from the top end to the bottom end, wherein the second slot forms a first opening of the second air channel and the aperture forms a second opening of the second air channel.

12. The electronic lighting device of claim 11, wherein the door is configured to obstruct at least one of the air channel and the second air channel.

13. The electronic lighting device of claim 10, further comprising a fan controller electrically coupled with the fan, and configured to vary a speed of the fan as a function of time, wherein the fan controller is programmed to operate the fan at full speed when the fan is powered on for a first predetermined time period, then power off the fan for a second predetermined time period, and then power on the fan to a fan speed between 50-80% of the full speed for a third predetermined time period.

14. An electronic lighting device, comprising:
an outer cover having a top end and a bottom end that at least partially define an internal cavity;
a housing disposed within the internal cavity at the top end, wherein the housing comprises an aperture;
a fan disposed within the outer cover;
first and second slots disposed on the bottom end that are each configured to receive a scent cartridge;
an air channel disposed from the top end to the bottom end, wherein the first and second slots form first and second openings, respectively of the air channel and the aperture forms a third opening of the air channel;
a movable door configured to selectively obstruct a path of air from the first or second slots to the air channel; and
a second air channel disposed from the top end to the bottom end, wherein the second slot forms a first opening of the second air channel and the aperture forms a second opening of the second air channel;
wherein the door is coupled to an actuator configured to move the door from a first position to a second position, and wherein the door obstructs the air channel in the first position, and the door obstructs the second air channel in the second position.

15. An electronic lighting device, comprising:
an outer cover having a top end and a bottom end that at least partially define an internal cavity;
a housing disposed within the internal cavity at the top end, wherein the housing comprises an aperture;
a fan disposed within the outer cover;
first and second slots disposed on the bottom end that are each configured to receive a scent cartridge;
an air channel disposed from the top end to the bottom end, wherein the first and second slots form first and second openings, respectively of the air channel and the aperture forms a third opening of the air channel;
a movable door configured to selectively obstruct a path of air from the first or second slots to the air channel; and
feet extending from the bottom end, wherein the feet are configured to slide inwardly within the outer cover from a first position to a second position when the top end of the outer cover receives a downward force, and wherein movement of the feet to the second position causes the fan to turn on or off.

* * * * *